United States Patent [19]

Tius et al.

[11] Patent Number: 5,633,357
[45] Date of Patent: *May 27, 1997

[54] SYNTHESIS OF CARBOXYLIC ACID GLUCURONIDES

[75] Inventors: Marcus A. Tius, Kailua; Mark R. Hagadone, Honolulu, both of Hi.

[73] Assignee: Synthetic Technology Corporation, Honolulu, Hi.

[ * ] Notice: The term of this patent shall not extend beyond the expiration date of Pat. No. 5,292,899.

[21] Appl. No.: 206,019

[22] Filed: Mar. 4, 1994

Related U.S. Application Data

[62] Division of Ser. No. 800,501, Nov. 27, 1991, Pat. No. 5,292,899.

[51] Int. Cl.$^6$ .................................................. C07H 1/00
[52] U.S. Cl. ........................... 536/18.5; 536/4.1; 536/7.1; 536/18.6; 549/388; 549/390; 549/393
[58] Field of Search .................... 536/4.1, 7.1, 18.5, 536/18.6; 549/388, 390, 393

[56] References Cited

U.S. PATENT DOCUMENTS

| | | | |
|---|---|---|---|
| 4,680,121 | 7/1987 | Ramsden | 210/635 |
| 4,833,073 | 5/1989 | Mc Nally et al. | 435/7 |
| 4,990,458 | 2/1991 | Rosenfeld | 436/174 |
| 5,036,014 | 7/1991 | ElSohly et al. | 436/8 |
| 5,137,626 | 8/1992 | Parry et al. | 210/198.2 |

FOREIGN PATENT DOCUMENTS

| | | |
|---|---|---|
| 90106444.4 | 10/1990 | European Pat. Off. ........ G01N 33/94 |
| 90111061.9 | 12/1990 | European Pat. Off. ........ G01N 33/94 |

OTHER PUBLICATIONS

Law et al. *J. Pharmacol.* 1984, 36(5), 289–94.
Fahrenholtz et al. *J. Am. Chem. Soc.* 1967, 89, 5934.
Bradow et al. *Chem. Res. Toxicol.* 1989, 2(5), 316–24; CA 111:166705u.
ElSohly et al. *J. Anal. Toxicol.* 1990, 14(5), 277–9; CA114:55169q.
Wall et al. *Marihuana '84, Proc. Oxford Symp. Cannabis* 1985, 69–76; CA 104:14455e.
Williams et al. *J. Pharm. Pharmacol.* 32: 445 (1980).
Razdan et al. *J. Am. Chem. Soc.* 96: 5860 (1974).
Hardrick et al. *Tetrahedron Lett* 681 (1979).
Mechoulam et al. *J. Am. Chem. Soc.* 94:6159 (1972).
Schwartz et al. *J. Org. Chem.* 51: 5463 (1986).
Pallante et al. *Drug Metab. and Disposition* 6: 389 (1978).
Tius et al. *J. Chem. Soc., Chem. Commun.* 62 (1989).
Cook, C.E. In: Cannabinoid Analysis in Physiological Fluids, *A.C.S. Symposium Series* 98, (Vinson, J.A., Ed.) A.C.S., Wash. D.C. 1979, pp. 137–154.
Teale, J.D. *Lancet* 2: 553 (1974).
Rodgers, R. et al. *Clin. Chem.* 24: 95 (1978).
Teale et al. *Nature* 249: 154 (1974).
Foltz, R.L. et al. *Biomed Mass Spectrom.* 10: 316 (1983).
Halcomb, R.L. and S.J. Danishefsky, *J. Am. Chem. Soc.*, 111: 6661–6666, 1989.
Kanaoka, M., S. Yano, H. Kato and T. Nakada, *Chem. Pharm. Bull.*, 34: 4978–4983, 1986.

*Primary Examiner*—Gary L. Kunz
*Assistant Examiner*—Kathleen Kahler Fonda
*Attorney, Agent, or Firm*—Christensen O'Connor Johnson & Kindness PLLC

[57] ABSTRACT

A method of producing a carboxylic acid glucuronide by reacting a carboxylic acid precursor with a blocked sugar epoxide precursor is disclosed. Also disclosed are: deuterated 11-nor-$\Delta^8$- or $\Delta^9$-THC carboxylic acid glucuronide having a deuterated hydrocarbon chain; 5'-deuterated 11-nor-$\Delta^8$- or $\Delta^9$-THC-carboxylic acid or 5'-deuterated $\Delta^8$- or $\Delta^9$-THC glucuronide. The compositions are useful as GC-MS standards; in methods for preparing antibodies reactive with a THC glucuronide; and, in GC-MS diagnostic methods for THC metabolites.

5 Claims, 5 Drawing Sheets

Scheme III

SYNTHESIS OF CARBOXYLIC ACID GLUCURONIDES

This is a divisional of application Ser. No. 07/800,501, filed on Nov. 27, 1991, U.S. Pat. No. 5,292,899.

FIELD OF THE INVENTION

This invention relates to methods for chemical synthesis of tetrahydrocannabinoid carboxylic acid glucuronides, to deuterated and undeuterated tetrahydrocannabinoid carboxylic acid glucuronides, to analytical standards and calibrators for diagnostic assays and to therapeutic compositions.

BACKGROUND OF THE INVENTION

Plants of the hemp family Cannabis produce significant amounts of cannabinoids. The compound $\Delta^9$-tetrahydrocannabinol ($\Delta^9$-THC) is an important cannabinoid which produces psychotrophic effects attributed to marijuana, hashish, and hash oil. Human metabolism of $\Delta^9$-THC results in microsomal oxidation through 11-hydroxy-$\Delta^9$-THC to a series of polar metabolites with 11-nor-$\Delta^9$-THC-9-carboxylic acid being a primary metabolite. The 11-nor-$\Delta^9$-THC-9-carboxylic acid is further catabolized to an ester-linked glucuronide, 11-nor-$\Delta^9$-THC-9-carboxylic acid glucuronide, that is excreted in urine and feces (see citation 1, infra).

Synthetic routes to $\Delta^9$-THC and its metabolites have been described previously (1–10). Although several approaches to the synthesis of 11-nor-$\Delta^9$-THC-9-methanol and 11-nor-$\Delta^9$-THC-9-carboxylic acid (1–11) have been described, the published syntheses are either time-consuming, produce racemic products, or give low yields. Recently the inventors disclosed an improved convenient synthesis of 11-nor-$\Delta^9$-THC-9-methanol (13). An enzymatic approach for synthesis of small amounts of impure 5'-hydroxy-$\Delta^9$- THC and 11-nor-$\Delta^9$-THC-9-methanol has also recently been disclosed (12).

THC glucuronide metabolites are present in biological fluids in vanishingly small amounts. These compounds are sensitive to electrophiles and extremely labile toward nucleophiles, making their preparation and isolation very difficult. The glucuronide carboxylic acid ester linkage is particularly labile to nucleophilic attack making chemical synthesis of this linkage extraordinarily difficult (14–16). Because of the lability of the THC-carboxylic acid linked glucuronides (THC glucuronides), it has not proven feasible to prepare sufficient quantities for use as assay calibrators or standards, or for use in the production of antibodies for immunoassays. THC glucuronides are a most useful class of therapeutic and diagnostic reagents and it would be highly advantageous to have a source of quantifies of highly-purified THC glucuronides.

Administration or use of marijuana or other products of the Cannabis plant can be detected through the analysis of biological fluids, such as blood or urine, e.g., in assays for $\Delta^9$-THC, $\Delta^9$-THC-9-carboxylic acid, or $\Delta^9$-THC-carboxylic acid glucuronide. Immunoassays are most widely used for this purpose (17–34), however, because of a significant number of false positive results, the immunoassay findings are frequently confirmed by gas chromatography-mass spectroscopy (GC-MS). GC-MS is useful for both confirmation and quantitation of THC (35–37). Deuterated derivatives of 11-nor-$\Delta^9$-THC-9-carboxylic acid (THC carboxylic acid) are commonly used as internal standards for GC-MS. Several problems are associated with the use of these deuterated THC carboxylic acids as standards. First, the deuterated THC carboxylic acid derivatives are relatively difficult to prepare and are expensive. Second, the base peak of the commonly used methyl-derivative is at m/z 316 and although the peak for the natural THC metabolite is at m/z 313, there is also a confusing peak at 316. Third, current methods for detection of the THC glucuronide metabolite require hydrolysis of the THC glucuronide metabolite, (i.e., within the GC-MS matrix), and the fragmentation pattern of the hydrolyzed product is then compared with that of a THC carboxylic acid standard. Hydrolysis efficiency in biological samples is highly variable, and dependent upon complex matrix effects and container wall effects, so that recovery, and detection limits of the GC-MS assay vary from sample to sample. Fourth, use of THC carboxylic acid as a standard does not provide an internal standard (i.e., for quantifying hydrolyis and ionization efficiency) for assessing the accuracy, precision, and detection limits of the GC-MS assay. As a result of these problems, a THC sample that has tested positive in an immunoassay, may test negative in a GC-MS assay. In view of the foregoing and other problems associated with the use of 11-nor-$\Delta^9$-THC-9-carboxylic acid it would be highly desirable to be able to eliminate false test results and solve problems relating to the lack of suitable THC analytical standards. Novel THC glucuronide analytical standards and calibrators for testing THC metabolites in biological fluids would be highly desirable.

Objects of the invention provide processes for chemical synthesis of THC glucuronides, (including 11-nor-$\Delta^9$-THC-9-carboxylic acid glucuronide), that are useful as immunogens for evoking antibodies, and as assay standards and calibrators in assays for detection and quantitation of THC metabolites in biological fluids. Other objects of the invention provide deuterated THC glucuronides, (e.g. deuterated-11-nor-$\Delta^9$-THC-9-carboxylic acid glucuronides), that are useful as internal standards and assay calibrators in GC-MS assays. Still other objects of the invention provide improved GC-MS assays using deuterated THC glucuronides with undeuterated THC glucuronides as internal standards to improve specificity, accuracy, precision, and detection limits of the GC-MS assays. Further objects of the invention provide methods for quantifying recovery of THC metabolites in biological samples that are useful on a sample-by-sample basis. The quantification of recovery allows the detection limits of the assay to be adjusted lower or higher until the desired precsion is reached. Such methods allow detection of THC metabolites in biological fluids with greater precision, specificity, and sensitivity and with fewer false-negative test results.

SUMMARY OF THE INVENTION

Embodiments of the invention provide methods of producing a deuterated or undeuterated 11-nor-$\Delta^8$-THC glucuronide or deuterated or undeuterated 11-nor-$\Delta^9$-THC glucuronide by reacting a blocked THC carboxylic acid precursor with a dual-blocked sugar epoxide precursor. Blocking of potentially reactive groups in the precursor compounds is accomplished with two protective agents: namely, a first protective agent that is a weak nucleophilic protective agent such as benzyl; and, a second protective agent that is an easily removable protective agent such as TBDMS. Other embodiments of the invention provide methods for removing the first and second protective agents by mild procedures that do not destroy the THC glucuronide product of the synthesis.

In other embodiments, the invention provides deuterated 11-nor-$\Delta^8$- or $\Delta^9$-THC carboxylic acid glucuronide, e.g.

11-nor-$\Delta^8$- or $\Delta^9$-THC-9-carboxylic acid glucuronide, that is deuterated in a hydrocarbon side chain of the cannabinoid ring. A preferred embodiment of the invention provides a 5'-deuterated 11-nor-$\Delta^8$- or $\Delta^9$-THC carboxylic acid, e.g. 5'-deuterated 11-nor-$\Delta^8$- or $\Delta^9$-THC-9-carboxylic acid, or a 5'-deuterated-$\Delta^8$- or $\Delta^9$-THC glucuronide, e.g. 5'-deuterated 11-nor-$\Delta^8$- or $\Delta^9$-THC-9-carboxylic acid glucuronide. The compounds of the invention are useful as GC-MS standards for use in assays detecting THC or its metabolites, and are also useful in preparing specific immunoglobulins reactive with a THC glucuronide but not with a corresponding THC carboxylic acid.

In still other embodiments, the invention provides diagnostic methods for detecting a metabolite of a cannabinoid in a biological fluid by using a THC glucuronide GC-MS standard, e.g., a deuterated or undeuterated 11-nor-$\Delta^9$-THC-9-carboxylic acid glucuronide.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As used herein the following terms have the meanings as indicated:

"THC metabolite" means a $\Delta^8$- or $\Delta^9$-tetrahydrocannabinol and the catabolic products of these compounds, including conjugation products such as the glucuronides.

"Blocked THC carboxylic acid precursor" means a chemically synthesized derivative of a $\Delta^8$- or $\Delta^9$-tetrahydrocannabinol of the general formula I:

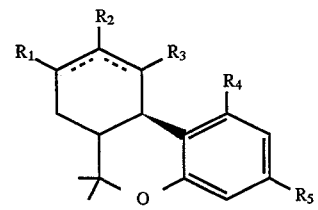

I wherein one of $R_1$, $R_2$, $R_3$, and $R_4$ comprises a carboxyl group and the remainder of $R_1$, $R_2$, $R_3$, and $R_4$ comprise either hydrogen atoms, or one or more hydroxyl groups blocked by a protective agent; $\Delta^8$ and $\Delta^9$ comprise different anomeric linkage in double bonding between the carbon atoms substituted with $R_1$ and $R_2$, or $R_2$ and $R_3$ ( i.e., the dashed line [ - - - ]); and, $R_5$ is a hydrocarbon chain comprising at least one carbon atom, e.g. Formula 5, FIG. 1.

"THC carboxylic acid" means a natural or chemically synthesized compound of the general formula I, wherein one of $R_1$, $R_2$, $R_3$, and $R_4$ comprises a carboxyl group and the remainder of $R_1$, $R_2$, $R_3$, and $R_4$ comprise either hydrogen atoms, or one or more hydroxyl groups; $\Delta^8$ and $\Delta^9$ comprise different anomeric linkage in double bonding between the carbon atoms substituted with $R_1$ and $R_2$, or $R_2$ and $R_3$ (i.e., the dashed line [ - - - ]); and, $R_5$ comprises a hydrocarbon chain comprising at least one carbon atom. In a preferred embodiment, the $R_5$ hydrocarbon chain is five carbon atoms in length and the positions of the carbon atoms are designated 1'–5' (i.e., as numbered sequentially in increasing order from the ring outward). A representative example of a THC carboxylic acid is provided by 11-nor-$\Delta^9$-THC-9-carboxylic acid.

Figure 1:
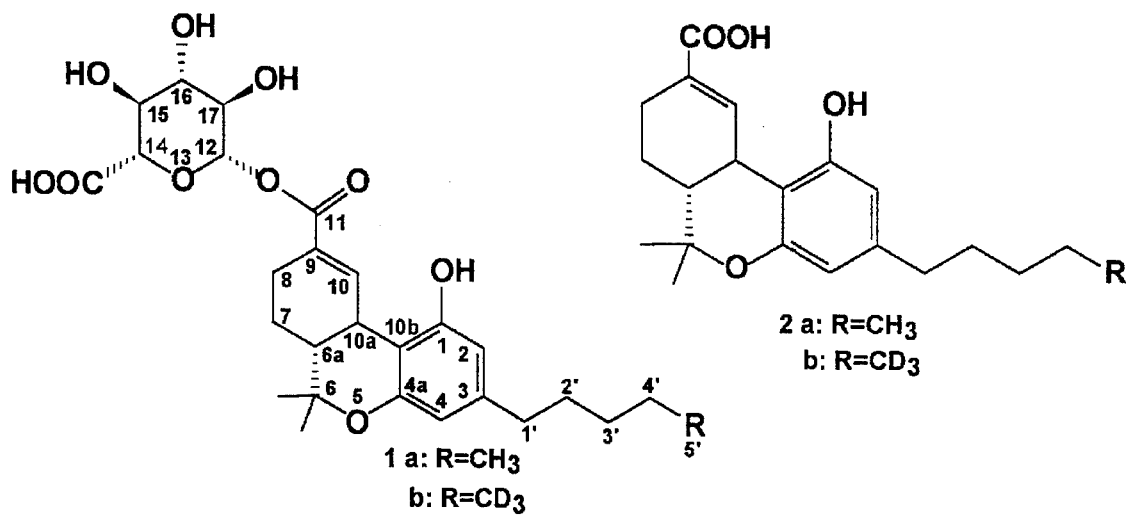
FIG. 1 depicts the chemical structures of intermediates (i.e. compounds of formulas 3a, 3b, 5a, 5b, 6) and reagents (i.e., compounds of formulas 4 and 7) used in chemical synthesis of deuterated ("D") and undeuterated ("H") 11-nor-$\Delta^9$-tetrahydro- cannabinol (THC)-9-carboxylic acid (the compounds of formulas 2b and 2a, respectively), and deuterated ("D") and undeuterated ("H") 11-nor-$\Delta^9$-tetrahydro- cannabinol (THC)-9-carboxylic acid glucuronide (the compounds of formulas 1a and 1b; as described in Examples 1-22 (below). Specifically, compounds 3a and 3b are 5'- undeuterated ("CH$_3$") and 5'-tri-deuterated ("CD$_3$"), respectively, 11-nor-$\Delta^9$-THC-9-carboxylic acid glucuronide blocked at the 1, 15 and 16 positions with three tert-butyl dimethyl silyl groups (TBDMS) and at the 14 carboxyl with a benzyl group (Bn). Compound 4 is glycal epoxide blocked at the 3 and 4 positions with TBDMS and at the 5 carboxyl group with Bn. Compound 5a and 5b are 5'undeuterated and deuterated, respectively, 11-nor-$\Delta^9$-THC-9-carboxylic acid blocked at the 1 position with TBDMS. Compound 6 is an intermediate 11-nor-$\Delta^9$-THC-9-carboxylic acid glucuronide blocked with TBDMS at the 1 position and Bn groups at the 15, 16, and 17 positions as well as at the 14 carboxyl. Compound 7 is a glucuronic acid blocked with Bn groups at the 2, 3, and 4 positions as well as at the 5 carboxyl.
Figure 1:
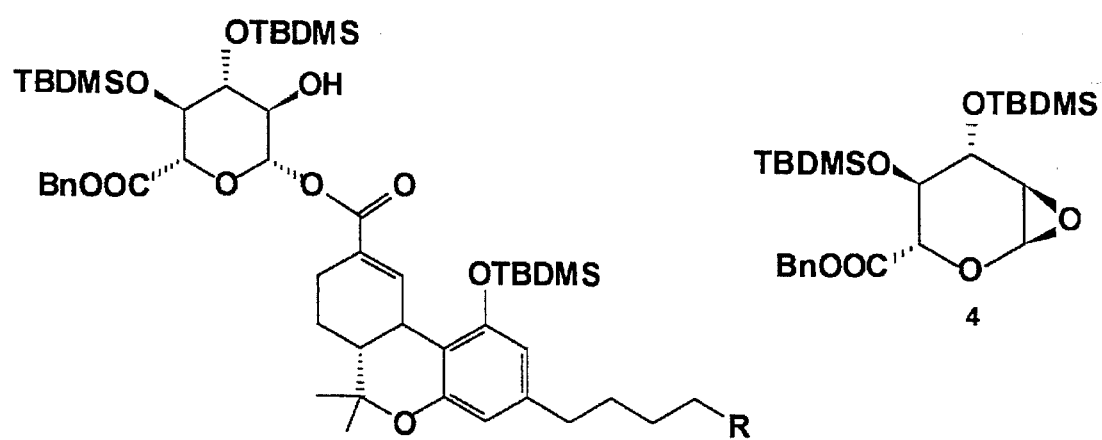
Figure 1:
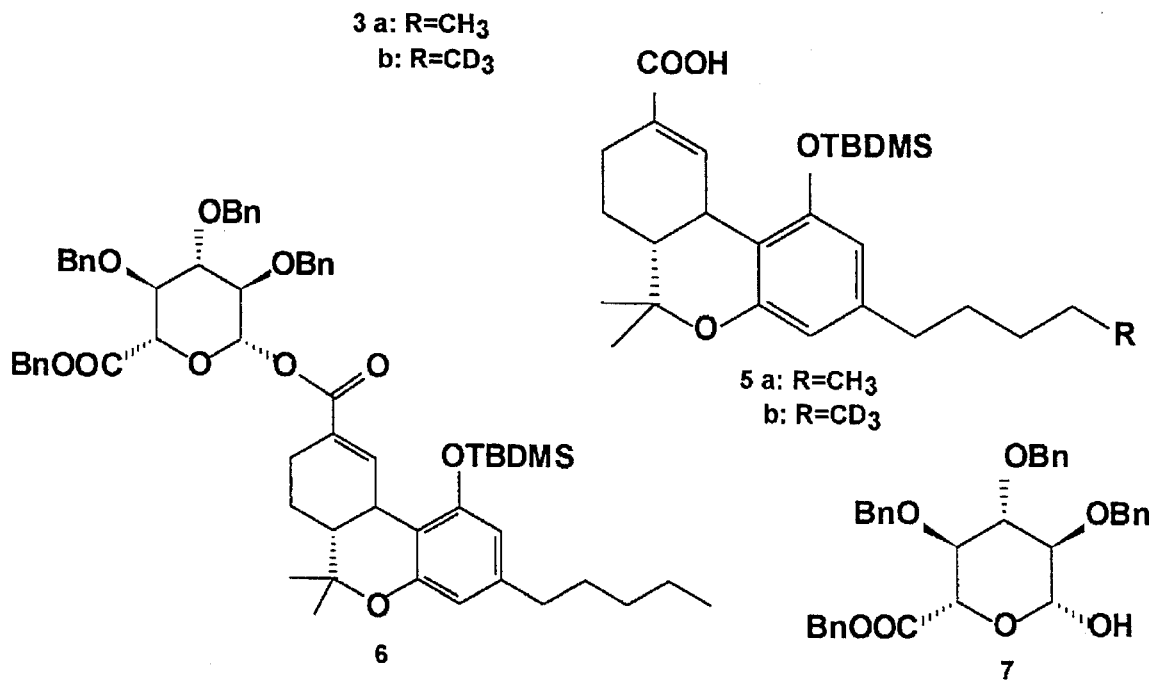

The term "11-nor-$\Delta^9$-THC-9-carboxylic acid" is used interchangeably herein with the term "$\Delta^9$-THC-carboxylic acid" to refer to a compound of the structure of Formula 2a, FIG. 1.

"Deuterated THC carboxylic acid" means a chemically synthesized THC carboxylic acid compound, as described above, wherein $R_5$ is a hydrocarbon chain of one or more carbon atoms substituted with one or more deuterium atoms.

"THC glucuronide" means a natural or chemically synthesized compound of the general Formula I, wherein one of $R_1$, $R_2$, or $R_3$ comprises a sugar-carboxyl group and the remainder of $R_1$, $R_2$, and $R_3$ comprise either hydrogen or hydroxyl groups; $R_4$ comprises a hydroxyl group; $R_5$ comprises a hydrocarbon chain comprising at least one carbon atom; further comprising a compound in which the sugar is a single or multiple ring structure, (e.g., glucose, galactose, maltose, lactose, and the like), and the sugar-carboxyl group forms an ester bond (i.e., through the carboxyl) to the carbon of the benzyl ring. A representative example of a THC glucuronide is provided by 11-nor-$\Delta^9$-THC-9-carboxylic acid glucuronide.

The terms "11-nor-$\Delta^9$-THC-9-carboxylic acid glucuronide", "$\Delta^9$-THC glucuronide", and "$\Delta^9$-THC-carboxylic acid glucuronide" are used interchangeable herein to refer to compounds with the structure of Formula 1a, FIG. 1.

"Deuterated THC glucuronide" as used herein means a chemically synthesized THC glucuronide compound, as described above, wherein at least one deuterium atom is bonded to at least one carbon atom, e.g. to a carbon atom in a benzyl ring or to a carbon atom in an R group of Formula I. A representative example is provided by tri-deutero-11-nor-$\Delta^9$-THC-9-carboxylic acid glucuronide, i.e., Formula 1b, FIG. 1, wherein three deuterium atoms are bonded to the carbon in the 5' position of the hydrocarbon chain comprising $R_5$.

"Blocked sugar" is used herein to refer to sugars of Formula II, below, having one or more protective agents blocking potentially reactive groups such as hydroxyl, carboxyl, aldehyde, and similar reactive groups during organic synthesis reactions. A representative example of a "blocked sugar" is provided by compound 10, FIG. 2; a representative example of a "dual blocked sugar", (i.e., a sugar blocked with two different types of protective agents that are blocking two different types of potentially reactive groups), is provided by compound 11, FIG. 2.

"Sugar epoxide" is used herein to refer to chemically reactive anhydro-sugar epoxide. A representative example is provided by 1,2 anhydro-glycal epoxide.

"Blocked sugar epoxide" is used herein to refer to a synthetic compound having one or more protective agents blocking potentially reactive groups on the sugar, e.g. hydroxyl or carboxyl groups. Blocked sugar epoxides may be conveniently synthesized from a "blocked sugar", (e.g. through a synthetic process such as that illustrated in Step "h" of FIG. 2, as described in Examples 7 and 10, below). "Dual-blocked sugar epoxide" and "dual-blocked sugar epoxide precursor" are used herein interchangeably to refer to a "blocked sugar epoxide" having a first protective agent, (e.g., a benzyl group), blocking a first potentially reactive group, (e.g., a carboxyl group), and a second protective agent, (e.g., a tert-butyldimethly silyl group, TBDMS), blocking a second potentially reactive group, (e.g., a hydroxyl group). A representative example of a "dual-blocked sugar" is provided by compound 4, FIG. 1.

"Protective agent" is used to refer to a class of chemical compounds that renders a potentially reactive group unreactive in a chemical reaction, and as such protective agents are useful for protecting potentially reactive chemical groups (e.g., OH, COOH, COH, and the like) from participating in irrelevant side-reactions during organic synthesis reactions. The process of protecting is referred to herein as "blocking", e.g., a reactive sugar hydroxyl or carboxyl group is "blocked" during synthesis of a THC glucuronide by the addition of a protective agent.

"Biological fluids" and "biological samples" are used synonymously to refer to fluids such as blood, serum, plasma, sputum, urine, fecal, hair and mucous samples as well as environmental samples such as soils, clothing, plastic and glass containers and the like.

Disclosed herein are new deuterated tetrahydrocannabinol (THC) carboxylic acids and deuterated and undeuterated THC glucuronides. Methods are also provided for the chemical synthesis of the deuterated THC carboxylic acids of the invention, as well as, for the deuterated or undeuterated THC glucuronides, as exemplified by deuterated 11-nor-$\Delta^9$-THC-9-carboxylic acid (e.g., compound 2b, FIG. 1) or deuterated or undeuterated 11-nor-$\Delta^9$-THC-9-carboxylic acid glucuronide (e.g., compounds 1a or 1b, respectively, FIG. 1).

The new deuterated THC carboxylic acids of the invention comprise a family of chemically synthesized THC carboxylic acid compounds of the formula I, above, wherein the $R_5$ group is a hydrocarbon chain that contains a carbon atom substituted with one or more deuterium atoms. In the case of compounds having more than one deuterium atom, the deuterium atoms may be bonded to the same carbon atom, e.g., in the hydrocarbon chain, or they may be bonded to multiple carbon atoms. Representative examples include mono-, di-, or tri-deuterated 11-nor-$\Delta^9$-THC-9-carboxylic acids. In a presently preferred embodiment of the invention, the $R_5$ group is five carbon atoms in length and three deuterium atoms are substituted to the 5' carbon atom of the hydrocarbon chain, i.e., compound 2b, FIG. 1.

Figure 4A:
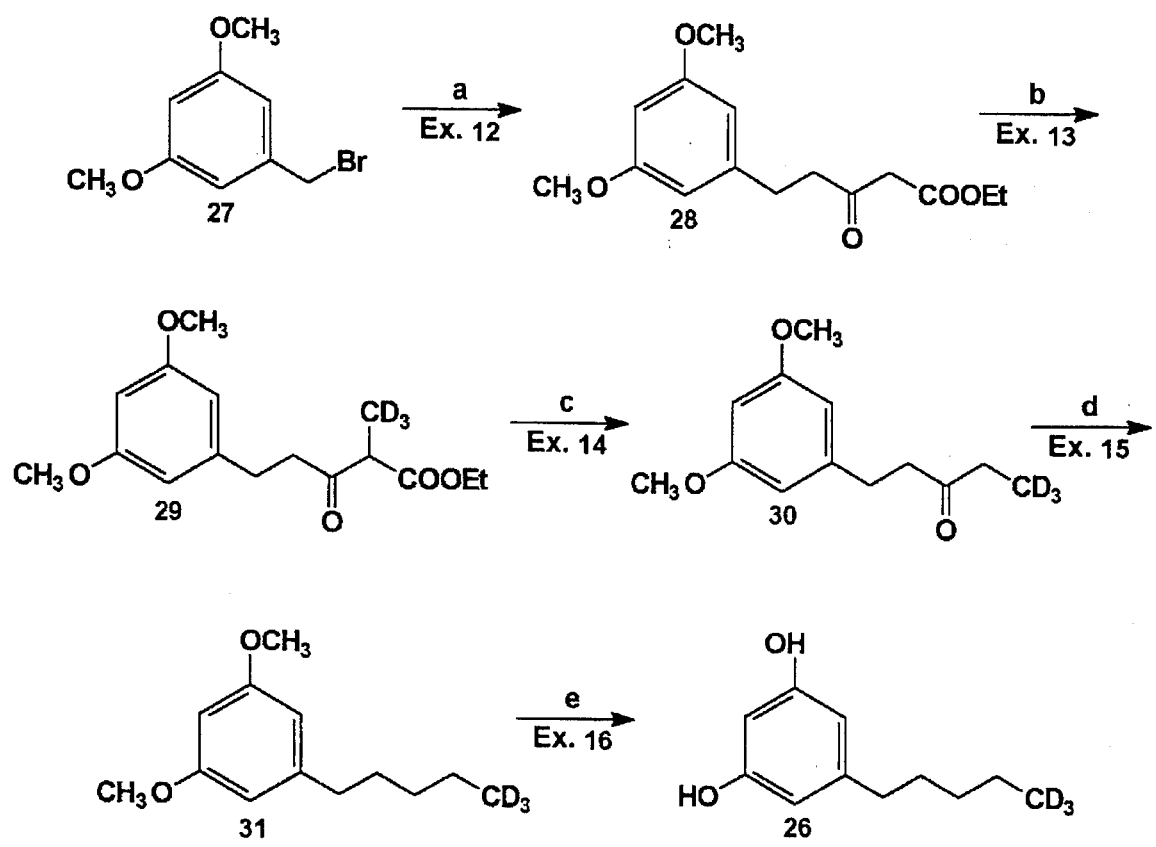
FIG. 4A depicts the first part of Scheme III (as described in Example 12 through Example 16, below) for chemical synthesis of deuterated-11-nor-$\Delta^9$-THC-9-carboxylic acid involving the reagents, conditions, and yields: (a) ethyl acetoacetate, NaH, n-BuLi, THF, 0° C., 75%; (b) NaH, CD$_3$I, THF, 0°–23° C., 78.7%; (c) NaOH, ethanol, reflux, 6 h, 94%; (d) TsNHNH$_2$, ethanol, reflux, 2 h; NaBH$_4$, methanol, reflux, 68.6%; (e) BBr$_3$, CH$_2$Cl$_2$, –78°–0° C., 96%.
Figure 4B:
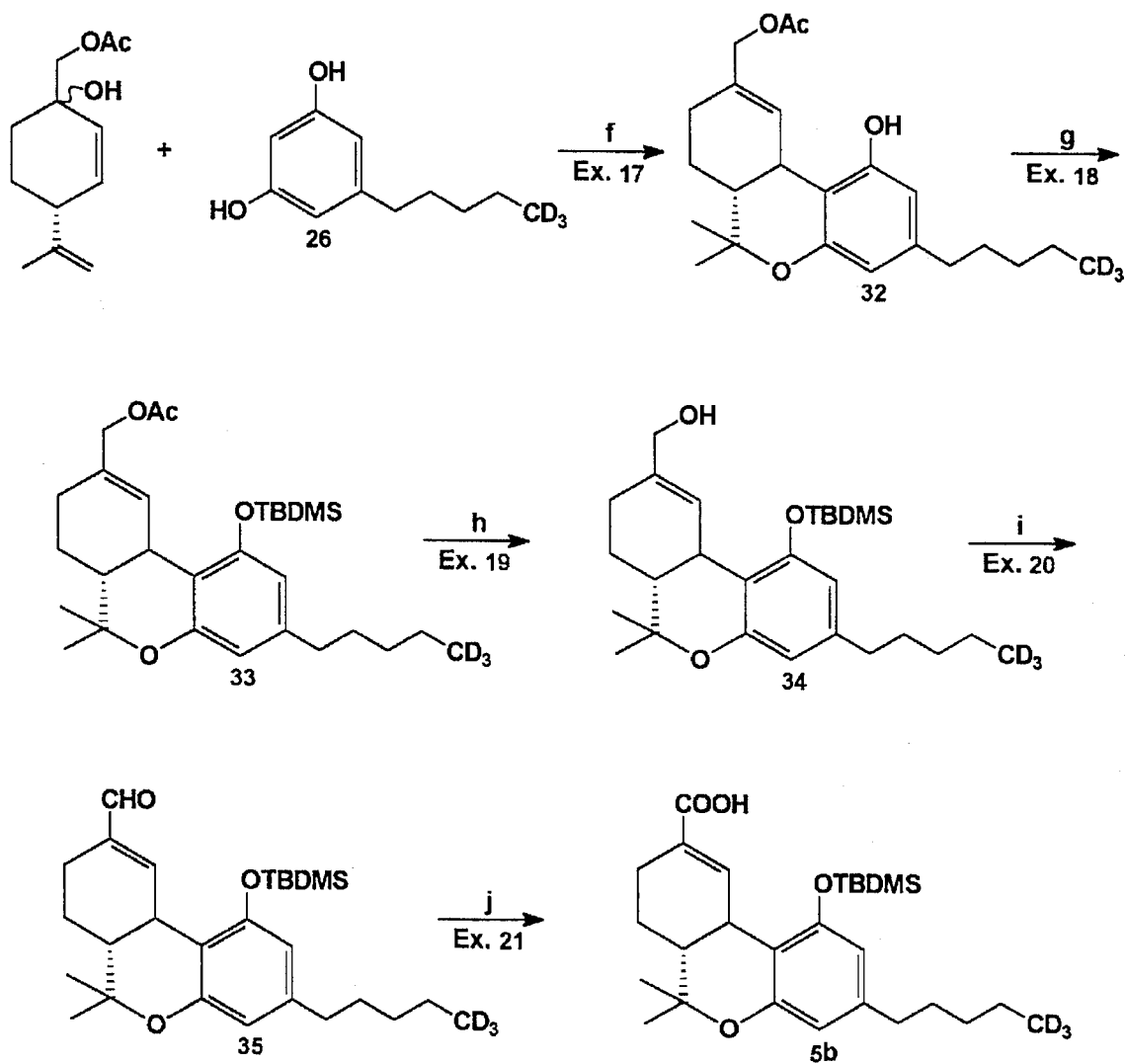
FIG. 4B depicts the second part of Scheme III (as described in Example 17 through Example 21, below) for chemical synthesis of deuterated-11-nor-$\Delta^9$-THC-9-carboxylic acid and the reagents, conditions, and yields: (a) catalytic BF$_3$·Et$_2$O, MgSO$_4$, CH$_2$Cl$_2$, 0°–23° C., 32.4%; (b) TBDMS-Cl, imidazole, DMF, 23° C., 88.2%; (c) lithium aluminum hydride, ether, 0°–23° C., 90%; (d) t-BuOMgBr, 1,1'-(azodicarbonyl)dipiperidine, THF, 23° C., 92%; (e) NaClO$_2$, t-BuOH, NaH$_2$PO$_4$, 2-methyl-2-butene, 23° C., 92%.

Embodiments of the invention provide methods for producing the deuterated THC carboxylic acids, above, in a stepwise manner similar to that described previously for synthesis of 11-nor-$\Delta^9$-THC-methanol (13), but modified and proceeding through the synthesis of a deuterated olivetol intermediate compound such as compound 26, FIG. 4a. Other embodiments provide methods for producing a blocked $\Delta^8$- or $\Delta^9$-THC-carboxylic acid that is for example useful in the synthesis of THC glucuronide. The synthesis of the blocked $\Delta^8$- or $\Delta^9$-THC-carboxylic acid comprises the steps of blocking the hydroxyl group of the No. 1 carbon of 11-nor-$\Delta^8$- or $\Delta^9$-THC-acetate, e.g., compound 32, FIG. 4B, with the second protective agent, e.g. TBDMS; followed by converting the acetate group of the blocked 11-nor$\Delta^8$- or $\Delta^9$-THC-acetate to a carboxylic acid. A representative example of a method for synthesis of a blocked THC carboxylic acid of the invention is provided by step "g" through step "j" depicted in FIG. 4B, and described in Examples 18 through 21, below. A representative example of the stepwise synthesis of a $\Delta^8$- or $\Delta^9$-THC-carboxylic acid is provided by step "a" through step "e", FIG. 4A, and step "f"

through step "j", FIG. 4B, as described in Example 12 through Example 21, below.

The new deuterated and undeuterated THC glucuronides of the invention comprise a family of THC derivative compounds of formula I, above, wherein $R_1$, $R_2$, $R_3$, $R_4$, and $R_5$ are as described above, and the compounds are optionally substituted with at least one deuterium atom. The deuterium atom(s) may be bonded to the carbon atom(s) of a benzyl ring, or to a carbon atom in $R_1$, $R_2$, $R_3$, $R_4$, or $R_5$ groups, above. In the case of compounds having more than one deuterium atom, the deuterium atoms may be bonded to the same carbon atom, or to multiple carbon atoms. Representative examples include mono-, di-, or tri-deuterated 11-nor-$\Delta^9$-THC-9-carboxylic acid glucuronide in which the deuterium atom(s) is bonded to the carbon atom at the 5' position, compound 1b, FIG. 1. The family of deuterated THC glucuronides of the invention comprises compounds in which a hydrocarbon chain comprising at least one carbon atom and one hydrogen or deuterium atom. In a presently preferred embodiment, the THC glucuronides comprise the compounds of formula I, wherein $R_5$ is a hydrocarbon chain of five carbons, and the 5' carbon atom is substituted with one or more deuterium atoms, i.e., 5'-deuterated 11-nor-$\Delta^9$-THC-9-carboxylic acid glucuronide.

Embodiments of the invention provide methods for producing the deuterated or undeuterated THC glucuronide of Formula I, above, by: a) reacting a deuterated or undeuterated blocked $\Delta^8$- or $\Delta^9$-THC carboxylic acid precursor (e.g., compound 2a, FIG. 1) blocked by a protective agent, (e.g. tert-butyldimethylsilyl, TBDMS, compound 5a, FIG. 1) with b) a dual-blocked sugar epoxide precursor (e.g., 1,2 anhydro-glycal epoxide; compound 4, FIG. 1), and then c) removing the protective agents (e.g., benzyl and TBDMS to obtain the THC glucuronide of Formula I, above, in which the carboxyl at either of $R_1$, $R_2$, or $R_3$ forms a carboxylic acid ester the linkage to the glycal. Presently preferred reaction conditions for carrying out the methods of the invention are provided below (i.e., see "Overview of Synthetic Scheme"). Representative conditions for the synthesis of the blocked THC carboxylic acid precursor and dual-blocked sugar epoxide precursor are also provided below (i.e., see "Choice of Protective Agents").

Representative examples of undeuterated and deuterated blocked THC carboxylic acid are provided by compounds 5a and 5b, respectively, shown in FIG. 1. In compounds 5a and 5b, the potentially reactive group, (i.e., the $R_4$ hydroxyl group of Formula I, above) corresponds with the hydroxyl group at the No. 1 carbon of compound 2a, FIG. 1; and, in this case, the reactive group is blocked with a TBDMS protective agent.

A representative example of a dual-blocked sugar epoxide is provided by compound 4, shown in FIG. 1. Dual-protected sugar epoxides are conveniently synthesized from dual-blocked sugars (see, "Choice of Protective Agents", below). In a preferred embodiment a dual-blocked sugar, (i.e., a dual-blocked blocked 1,2 anhydro-glycal; compound 4, FIG. 1), is synthesized with a carboxyl group at the No. 5 carbon (as represented in Formula II, below) blocked by a first weak nucleophilic protective agent (e.g., a benzyl group) and with the hydroxyl groups at the No. 3 and No. 4 carbon atoms blocked by a second easily removable protective agent (e.g., tert-butyldimethylsilyl, TBDMS). The dual-protected sugar is then conveniently converted to the dual-protected sugar epoxide precursor (e.g., by step "h", FIG. 2, as disclosed in Examples 7 and 10, below).

In a preferred embodiment of the invention a deuterated 11-nor-$\Delta^8$ or $\Delta^9$-THC carboxylic acid glucuronide (i.e., THC glucuronide, above; e.g. compound 1a or 1b, FIG. 1) is provided having one or more deuterium atoms bonded to one or more carbon atoms in the hydrocarbon chain at the $R_5$ position (Formula I, above). In a presently most preferred embodiment, the hydrocarbon chain is five carbons in length and one or more deuterium atoms are bonded to the 5' carbon of this chain, (i.e., one deuterium as used herein is referred to as "mono-deuterated"; two, "di-deuterated"; three, "tri-deuterated", etc.).

In another preferred embodiment of the invention a method is provided for stepwise removal of the first protective agent (e.g., the benzyl group at carbon No. 14, compound 3, FIG. 1) and the second protective agent, (e.g., TBDMS from the hdyroxyl at carbon No. 1, compound 3, FIG. 1, and also from the sugar hydroxyl groups at carbon No. 15 and No. 16 of compound 3, FIG. 1) to obtain the THC glucuronide (e.g., 11-nor-$\Delta^8$- or $\Delta^9$-THC-carboxylic acid glucuronide; compound 1a, FIG. 1). In a presently most preferred embodiment of the invention the first protective agent (e.g. a benzyl group) is removed by a mild procedure such as catalytic hydrogenation (e.g., step "k", FIG. 2) that does not destroy the THC glucuronide, and the second protective agent (e.g. TBDMS) is removed by a procedure such as by addition of HF and $CH_3CN$ at 0° C. (e.g., step "j", FIG. 2) that avoids use of a Lewis base, and does not generate byproducts.

An overview of the synthetic scheme is disclosed first, followed by procedures for the choice of suitable protective agents for blocking the potentially reactive groups, (i.e., in the THC carboxylic acid and the dual-blocked sugar precursors), followed by procedures for use of the THC glucuronides of the invention in the production of specific antibodies (Example 24), e.g. for use in immunoassays (Example 24), and for calibrators and analytical standards in improved gas chromatography-mass spectrometry (GC-MS) assays that measure THC metabolites in biological fluids (Example 22–23).

Overview of Synthetic Scheme

Figure 2:
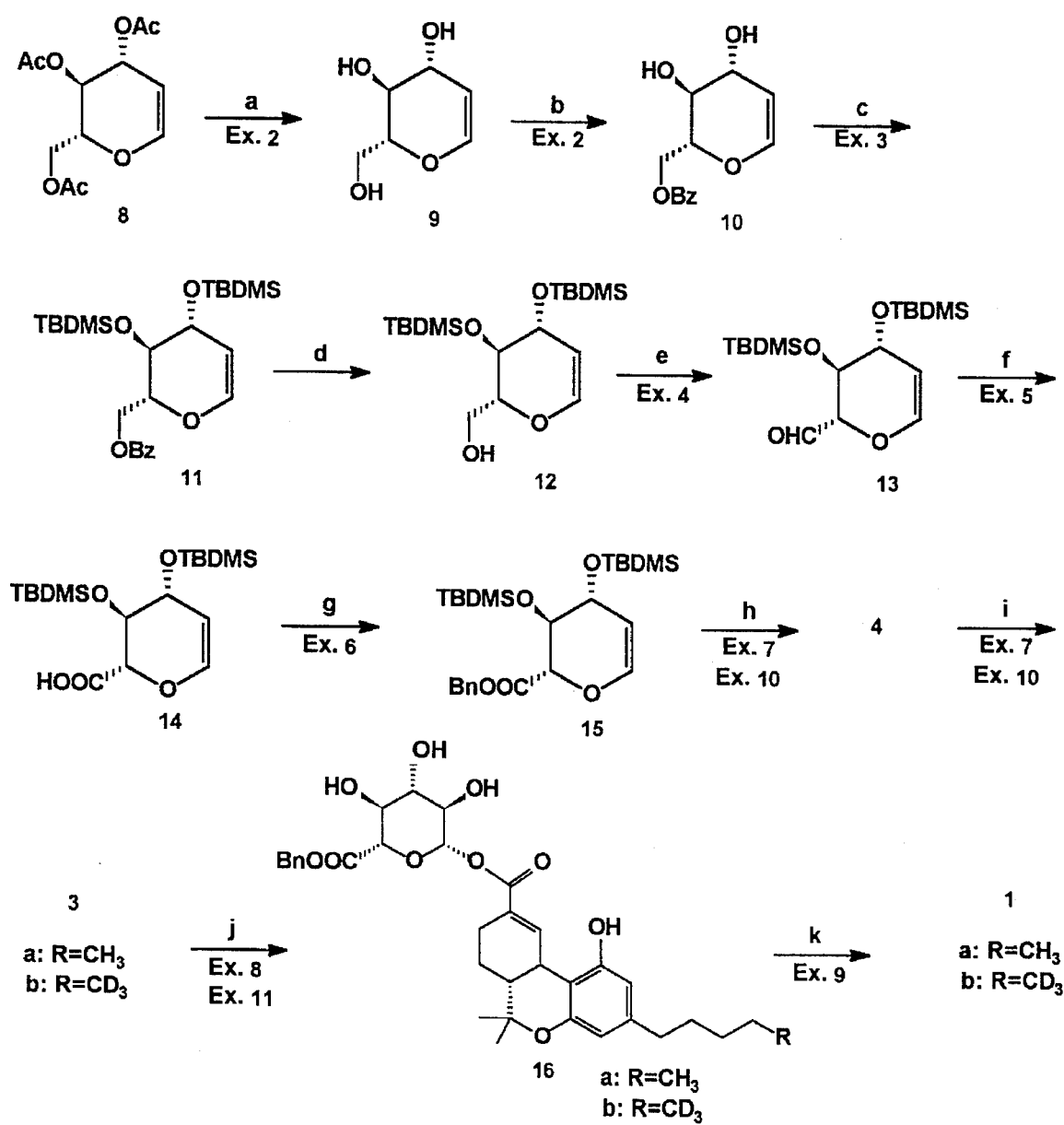
FIG. 2 depicts Scheme I (as described in Examples 2 through Example 9, below) for a presently preferred method for the chemical synthesis of 11-nor-$\Delta^9$-THC-9-carboxylic acid glucuronide (1) through the steps of "a" to "k", below, involving the following reagents, conditions, and yields: (a) K$_2$CO$_3$, CH$_3$OH, 23° C.; (b) ArCOCl, pyridine, 0°–23° C., 67.8% overall yield; (c) TBDMS triflate, Et$_3$N, CH$_2$Cl$_2$, 0° C., quantitative yield; (d)LiAlH$_4$, ether, 0° C., 90%; (e) t-BuOMgBr, 1,1'-(azodicarbonyl)dipiperidine, THF, 23° C.; (f) NaClO$_2$, t-BuOH, NaH$_2$PO$_4$, 2-methyl-2-butene, 23° C., 34% overall yield; (g) benzyl alcohol, DCC, DMAP, DMAP HCl, CHCl$_3$, 91%; (h) dimethyl dioxirane, CH$_2$Cl$_2$, 0° C.; (i) 5a, THF, 24 h, 57% of 3a; 5b, 48 h, 72% of 3b; (j) aq. HF, CH$_3$CN, 0° C., 33% of 16a and 62% of 17a; 47% of 16b and 49% of 17b; (k) H$_2$ atmosphere, Pd (10% on carbon) ethyl acetate, quantitative yield.

An overview of a scheme for synthesis of a representative THC glucuronide is shown in FIG. 2, as described Example 1, below. Details of the reaction conditions, mass spectroscopic (MS) and infra-red (IR) spectral properties of the products, and yields are provided in Examples 2–21, below.

A brief discussion of a representative chemical synthesis of a THC glucuronide, e.g. 11-nor-$\Delta^9$-tetrahydrocannabinol-9-carboxylic acid glucuronide, follows. (Details of reaction conditions for synthesis of a 11-nor-$\Delta^9$-THC-9-carboxylic acid precursor are presented in Example 12 through Example 21, below; reaction conditions for synthesis of a dual-blocked sugar epoxide precursor appear in Examples 2–7, below; and, details of the synthesis of a 11-nor-$\Delta^9$-THC-9-carboxylic acid glucuronide product are presented in Example 2 through Example 9, below.)

Preferrably each of the two parts of the THC glucuronide compound, i.e., the dual-blocked sugar epoxide and the oxidized blocked cannabinoid, are conveniently synthesized separately. Synthesis of the dual-blocked sugar epoxide precursor will be illustrated first, followed by synthesis of the blocked THC carboxylic acid precursor.

A representative method for synthesis of a dual-blocked sugar epoxide precusor is detailed below in Examples 2–7, below. In this illustrative organic synthesis scheme the conjugated bond system of the sugar is removed and replaced to form a 1,2 glycal; any reactive acetyl, carboxyl, or aldehyde group and the like in the sugar is blocked with a first protective agent, e.g. by converting the group to a carboxyl group and then forming an ester linkage with a weak nucleophilic protective agent, (e.g., a benzyl group). In addition, any available reactive hydroxyl groups in the sugar are also blocked, but with an easily removable protective agent (e.g., TBDMS) rather than a nucleophilic protective agent. With certain sugar starting materials it may prove desirable to remove the first protective agent, (e.g., the benzyl group at the 5 carbon of the ring; Formula II, below) and convert the resultant hydroxyl group through an aldehyde to a carboxyl group (e.g., Steps "d–f", FIG. 2; Examples 4–6, below). In this manner the carboxyl group which will ultimately appear in the glycal ring of the THC glucuronide is formed (e.g., position 14, of THC glucuronide compound 1a and 1b, FIG. 1). The newly formed carboxyl is then re-blocked with the first protective agent, (e.g., forming a benzyl-ester, compound 15, FIG. 2), before reacting the blocked sugar with a dioxirane (e.g., dimethyl dioxirane, step "h", FIG. 2 and Examples 7 and 10, below) to form the dual-blocked sugar epoxide precursor (e.g., compound 4, FIG. 1).

Representative starting materials for synthesis of a dual-blocked sugar epoxide are single or multiple ring sugars such as glucose, galactose, xylose, maltose, lactose, and the like. Representative examples of intermediates in the synthesis of the dual-blocked sugar epoxide are as follows: 1) compound 8, FIG. 2 is representative of a 1,2 glycal lacking the conjugated bond system of the sugar; 2) compound 10, FIG. 2 is representative of a blocked sugar with a potentially reactive acetyl groups at the 5 carbon of the ring converted to a hydroxyl groups and then blocked with a first protective agent, (e.g., by forming a benzyl ether); 3) compound 11, FIG. 2 is representative of a dual-blocked sugar with the hydroxyl groups at the 3 and 4 carbons of the ring blocked with a second protective agent, (e.g., with TBDMS); 4) compound 13, FIG. 2 contains a potentially reactive aldehyde gorup that is convented to a potentially reactive carboxyl group in compound 14, FIG. 2 before blocking reactivity by forming an ester with the first protective agent (e.g., benzyl-ester); and, 5) compound 4, FIG. 1 is representative of a dual-blocked sugar epoxide precursor. The dual-blocked sugar is converted to a sugar epoxide precursor, e.g. the 1,2 anhydro-glycal epoxide precursor, by treatment with a dioxirane through a procedure such as that illustrated in Step "h", FIG. 2, and as described in Examples 7 and 10, below.

Embodiments of the invention provide methods for synthesis of a blocked THC carboxylic acid precursor (e.g. compound 5a, FIG. 1). A blocked THC carboxylic acid may be synthesized by procedures such as those outlined below in Examples 12–21, below. The synthesis may be accomplished by the steps of blocking any reactive hydroxyl groups in a THC carboxylic acid (e.g. at the $R_4$ hydroxyl of Formula I; corresponding to the hydroxyl at carbon No. 1 in compound 2a, FIG. 1).

The following procedures are provided to identify certain key features of the synthetic scheme of the invention that are worthy of consideration by skilled artesans. Those skilled artesans will recognize these considerations as providing useful information for organic synthesis of a blocked sugar epoxide precursor, and a blocked THC carboxylic acid precursor: namely, 1) For protecting the reactive sugar carboxyl and hydroxyl groups (i.e., at positions R1, R2, and R3, Formula II, below) a weak nucleophilic blocker (e.g. a benzyl group) may be desirable for blocking the $R_1$ carboxyl,, while an easily-removable blocker (e.g. tert-butyl dimethyl silyl; TBDMS) may be desirable at the $R_2$ and $R_3$ hydroxyl groups ( Formula II, below). The desirable properties of protective agents are described below (see, Choice of Protective Agents). Desirable properties in the second protective agent are different than those of the first, i.e., the second protective agent may not be suitable for blocking the carboxyl group. For example, TBDMS is not sufficiently stable for use as a first protective agent, i.e., in blocking potentially reactive groups such as carboxyl, acetyl, or aldehyde, but is useful as a second protective agent, i.e., for blocking potentially reactive hydroxyl groups.

2) The endogenous carboxyl of the THC carboxylic acid is useful for catalyzing the reaction of the blocked sugar epoxide with the blocked THC carboxylic acid and it is generally undesirable to add an exogenous acid such as a Lewis acid as a catalyst because the acid must then be neutralized, e.g., with a Lewis base, and the THC glucuronide product of the reaction is unstable under these conditions. It is also difficult to purify the THC glucuronide from a mixture containing a Lewis acid.

3) In selecting conditions for removing the protective agents from the THC glucuronide product of the reaction, it is desirable that consideration be given to mild conditions by which this may be accomplished without destroying the highly labile carboxylic acid ester linkage to the sugar (e.g., glycal) group. Treatment with $HF/CH_3CN$ (Step "j", FIG. 2) is one such mild condition that removes TBDMS, and catalytic hydrogenation to remove benzyl is another such condition (e.g. Step "k", FIG. 2).

4) For purifying the THC glucuronide product of the synthesis, care must be taken not to destroy the relatively unstable THC glucuronide. One such method is by evaporative removal of toluene that is a volatile byproduct of the catalytic hydrogenation in "3", above.

Other embodiments of the invention provide synthetic methods that are generally applicable to synthesis of many different labile carboxylic acid ester-linked glucuronide compounds, (i.e., compounds other than THC glucuronides). For example, the methods of the invention may also be employed for preparing carboxylic acid ester-linked alternative glucuronides. Representative examples of alternative glucuronides include glucuronides of cocaine metabolites such as ecgonine or benzoylecgonine and the like. The synthesis of alternative glucuronides may conveniently be accomplished by reacting a blocked alternative carboxylic acid precursor with a blocked sugar epoxide precursor. Following the procedures provided above in "1" through "4" skilled artesans will recognize that starting materials for synthesis of alternative glucuronides are the respective alternative carboxylic acid precursor compounds, (e.g., ecgonene carboxylic acid), and that the synthesis will include blocking of potentially reactive sugar groups (e.g. carboxyl, aldehyde, acetal, and hydroxyl groups and the like) with a first protective agent, as described above, and blocking of potentially reactive groups in the alternative carboxylic acid compound (e.g. hydroxyls and the like) with a second protective agent, as described above. The synthesis of a dual-blocked sugar epoxide precurosr may be accomplished as described above.

Choice of Protective Agents

Positions at which protective groups, i.e., $R_5$, $R_6$, or $R_7$, are introduced to block the sugar hydroxyl groups and carboxyl group in synthesizing a dual-blocked sugar epoxide precursor, are represented in Formula II. The postions of the carbon atoms in the ring are represented with Arabic numerals 1 through 5.

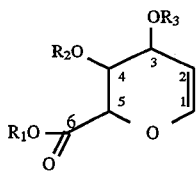

II

Embodiments of the invention provide methods for blocking potentially reactive groups in a sugar, (e.g., hydroxyl, acetyl, aldehyde, carboxyl groups, and the like), prior to synthesizing a dual-blocked sugar epoxide precursor, e.g. compound 4, FIG. 1. In considering the choice of protective agents those skilled in the art will recognize the desirability of considering the choice of protective agent in the context of the totality of the reaction conditions used in the organic synthesis, the stability of various intermediates, and the ease of purification of the final glucuronide product. An illustrative procedure by which such a synthesis may be accomplished is provided in Examples 2–9, below, as outlined schematically in FIG. 2. The synthetic scheme has also been discussed briefly above.

Selecting a first (e.g., benzyl) and a second (e.g., TBDMS) protective agent will be discussed next, followed by a general discussion of the reaction conditions in which a dual-blocked sugar epoxide may be reacted with a blocked THC carboxylic acid precursor to generate the THC glucuronide product of the reaction.

The correct choice of protective groups is a key to success of the method. It is necessary to use protective agents that are: a) unreactive in the synthesis sequence, b) without effect in changing the stereochemistry of the reaction, but c) removable without destroying the carboxylic-ester-linked THC glucuronide product of the synthesis. In general, it may be desirable that: 1) the first (i.e., carboxyl) protective agent be chosen to give a more robust, (i.e., less sensitive to electrophilic or nucleophilic attack and hydrolysis), chemical bonding than the second (i.e., hydroxyl) protective agent; 2) both the first and the second protective agent are stable in the synthetic sequence, yet easily-removable under mild conditions such that the relatively unstable product of the reaction, i.e., the THC glucuronide, is easily purified. For example, while TBDMS functions to protect the hydroxyl groups, silicon groups which are also easily removable, are not effective protective agents because they are too easily removable.

Representative examples of a first weak nucleophilic protective agent that may be useful for blocking reactive groups (e.g. carboxyl groups, aldehyde groups, acetyl groups and the like) in the synthesis of a dual-blocked sugar epoxide precursor are benzyl (e.g., by forming a stable benzyl ether or ester), methoxybenzyl, dimethoxybenzyl, cinnamyl, allyl, methallyl, trityl, fluorenyl, or diphenylmethyl groups and the like, and groups with the general formulas IIIa and IIIb, below.

*IIIa*=$C_6H_5CH=CHCH_2$

*IIIb*=$p\text{-}CH_3OC_6H_4CH_2$     III

Representative examples of a second easily-removable protective agent that may be useful for blocking reactive groups (e.g. hydroxyl groups) in synthesis of both a dual-blocked epoxide precursor and a blocked THC carboxylic acid precursor are substituted silyl ethers such as tert-butyl dimethyl silyl (TBDMS), tert-butyl dimethyl allyl (Formula IVa), t-hexyldimethylsilyl (Formula IVb), triethylsilyl (Formula IVc), and tri-isopropylsilyl (Formula IVd), i.e., the general formulas IVa,b,c, and d as represented in Formulas IVa–IVd, below.

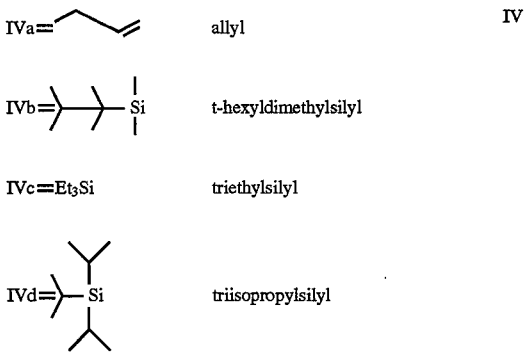

In a preferred embodiment of the invention, a benzyl group is employed as the preferred first protective agent (e.g. as the carboxyl protective agent) and TBDMS is employed as the preferred second protective agent (e.g. for hydroxyl groups). The combination of benzyl and TBDMS protective agents is preferred because: a) the TBDMS groups are stable to oxidation of the glucal to the epoxide; b) the reaction is a clean reaction, i.e., with no by products; c) the reaction gives a good yield of product; d) the benzyl group is easily removed under mild reaction conditions which do not affect the THC glucuronide product; and, e) the only by product of the reaction is toluene, which is easily removed under vacuum.

Conditions for Reacting the Blocked THC Carboxylic Acid Precusor with a Dual-Blocked Sugar Epoxide Representative conditions for reacting a dual-blocked sugar epoxide precursor (e.g., compound 4, FIG. 1) with a blocked THC carboxylic acid precursor (e.g., compounds 5a and 5b, FIG. 1) are described below, i.e., Step "h", FIG. 2, and Examples 7 and 10. Treatment of a dual-protected sugar with a dioxirane, (e.g., dimethyl dioxirane) produces a reactive sugar epoxide precursor which is immediately coupled to the blocked THC carboxylic acid precursor producing a dual-blocked-THC glucuronide (e.g., compound 3, FIG. 1). The conditions in this synthesis step can influence the yield of the final THC glucuronide product. For example, it is important not to use acid catalysis, e.g., with a Lewis acid such as employed previously by others (38), because the THC glucuronide product is acid labile, and purification to remove the acid is also extremely difficult. It is desirable for the carboxyl of the THC carboxylic acid to catalyze the reaction and fortunately, it does so, such that there is no catalytic Lewis acid required.

Following synthesis of the dual-blocked THC glucuronide, the first and second protecting agents may be removed sequentially, e.g., TBDMS may be removed with HF and $CH_3CN$ at 0° C. (Step "j", FIG. 2) and benzyl may be removed by catalytic hydrogenation (Step "k", FIG. 2). In this manner final THC glucuronide product, e.g., 11-nor-$\Delta^9$ THC-9-carboxylic acid glucuronide, compound 1a, FIG. 1, is produced.

Conditions for Removal of Protective Agents

Other embodiments of the invention provide methods by which the protective agents may be removed from the product THC glucuronides of the synthesis, while permitting simple purification of the glucuronide product. Those skilled in the art will recognize that removal of a Lewis acid (i.e., an electron acceptor such as the first or second protective agents) from a reaction mixture ordinarily requires the use of a base. However, the carboxylic acid-ester products are extremely labile under these conditions and, in the presence of a base, would undergo either hydrolytic cleavage of the ester or oxidation. Thus, it is desirable that the protective group be removable under conditions that do not alter or change the product. Catalytic hydrogenation (i.e., see Step "k", FIG. 2, and Example 9, below) or other similarly mild conditions are illustrative examples of processes useful for removing the protective agents from the glucuronide products of the synthesis.

Representative conditions for removal of the first protective agents of Formulas IIIa and IIIb are as follows: namely, a) The cinnamyl carboxylate (i.e., Formula IIIa) may be cleaved under nearly neutral conditions (e.g., Hg(OAc)$_2$, MeOH; KSCN, H$_2$O), but it will be recognized that this will make the purification of the THC glucuronide product more difficult, i.e., because the glucuronide is labile, and this will necessarily lead to a lower yield of product.

b) The p-methoxybenzyl carboxylate (i.e., Formula IIIb) may be cleaved by acidic hydrolysis (CF$_3$COOH/PhOMe, or HCOOH), but it will be recognized that this may cause problems in the purification of the THC glucuronide product because of the strong acidity of formic acid the by product of the reaction, i.e., p-methoxybenzyl alcohol.

Representative illustrative examples for removal of the second protective agents of Formulas IVa–IVd, above, are as follows: namely, a) The allyl group (i.e., Formula IVa) may be removed under mild conditions, e.g. HgCl$_2$/HgO, acetone-H$_2$O, and is a suitable replacement for TBDMS, however, those skilled in the art will recognize that there will be a problem in the oxidation of the glucal to the glucal epoxide.

b) The dimethylsilyl group (i.e., Formula IVb; which is most similar to TBDMS) may be conveniently removed under the same conditions as TBDMS, however, it will be recognized that a longer time will be required for the desilylation reaction, and that this will necessarily lead to lower yields of THC glucuronide product.

c) The Triethylsilyl group (i.e., Formula IVc) is more easily removable than TBDMS, but is removable under the same conditions as TBDMS, however, one skilled in the art will recognize that its use creates problems of stability during the Mukaiyama oxidation reaction.

d) The dimethylisopropylsilyl (i.e., Formula IVd) may not be sufficiently stable for the synthetic sequence, although it is suitable for use as an easily removable group. Thus, one skilled in the art will recognize that the reaction conditions may need to be modified to promote the use of this group as a protective agent.

Glucuronide Antigens, Analytical Standards, and Calibrators in Diagnostic Assays The availability of substantial quantities of highly-purified THC glucuronides provided by the practice of the invention, e.g. 11-nor-$\Delta^9$-THC-9-carboxylic acid glucuronide, provides for the first time a ready source of analytical calibrators and standards for use in testing biological fluids for the presence of THC metabolites. In one embodiment the invention provides either an undeuterated, or a mono-, di- or tri-deuterated 11-nor-$\Delta^9$-THC-9-carboxylic acid or its glucuronide that is useful as an analytical standard in GC-MS. In a preferred embodiment the deuterium atom (or atoms) is located in the hydrocarbon chain at the $R_5$ position of the compound of Formula I. In a most preferred embodiment, the deuterium atom (or atoms) is located at the 5' carbon of a five carbon hydrocarbon chain at the $R_5$ position of the compound of Formula I. The deuterated and undeuterated GC-MS standards of the invention are conveniently supplied in the form of reagents and test kits, which may be supplied with instructions for their use in improved methods for testing biological samples for the presence of THC metabolites. In one embodiment, an admixture of the deuterated THC and undeuterated THC glucuronide is formed in a biological fluid sample so that the deuterated THC compound of the invention serves as an internal calibrator, e.g., for quantifying recovery in the undeuterated standard in GC-MS assay. In another embodiment, the deuterated THC glucuronide of the invention is useful as a calibrator in a GC-MS assay procedure, or as a positive control standard, when mixed with a biological sample and introduced into GC-MS.

Other embodiments of the invention, provide improved assay procedures for measuring THC metabolites in biological samples. To describe the improvements offered by the invention it is desirable to first briefly provide an illustrative example of a current assay protocol for measuring THC metabolites in a biological fluid by GC-MS. For example, in one such assay procedure for cannabinoids, a deuterated GC-MS standard is mixed with a biological sample and the mixture is then commonly hydrolyzed, i.e., to convert the deuterium-labeled glucuronide and the natural metabolite into the same form. Because hydrolysis efficiency is significantly dependent upon matrix effects, actual recovery of the glucuronide varies in practice from one sample to another.

In the practice of the invention, deuterated or non-deuterated THC glucuronide standards are provided so that hydrolysis is not necessary, and so that the percentage recovery can be calculated in any sample. Thus, in one embodiment the invention provides an improved assay method for the determination of the presence or amount of a cannabinoid in a sample which a deuterated THC glucuronide, e.g., undeuterated, or a mono, di or tri-deuterated 11-nor-$\Delta^9$-THC-9-carboxylic acid glucuronide, is used as a GC-MS standard and calibrator to measure the % recovery from a biological sample. Practice of this embodiment of the invention provides improved simplicity, (i.e., by eliminating the hydrolysis step), improved assay performance, (i.e., improved specificity, sensitivity, precision), and a lower level of detection in assays for detection of THC metabolites. This is possible because the deuterated THC glucuronide and the natural metabolite, i.e., in the biological sample, are equivalent molecules and both are equivalently derivatized, i.e., by silyl groups, etc., during sample preparation for GC-MS. (Additional description is provided herein in Example 22, below.)

Other embodiments of the invention provide improved diagnostic methods for detecting cannabinoids in biological fluids by the steps of: a) adding a deuterated THC glucuronide GC-MS calibrator or standard, e.g., an undeuterated, or a mono, di or tri-deuterated 11-nor-$\Delta^9$-THC-9-carboxylic acid glucuronide to a biological sample; b) extracting the biological sample to collect the GC-MS standard and natural metabolite, e.g., with an organic solvent; c) derivatizing the standard and the natural metabolite, e.g., with a silyl group; and d) separating the sample on GC-MS. In this case the improvement is provided by adding a deuterated-THC glucuronide GC-MS compound, e.g., a mono, di or trideuterated 11-nor-$\Delta^9$-THC-9-carboxylic acid glucuronide, so that hydrolysis is not required prior to the GC-MS step. The improved diagnostic methods of the invention provide greater sensitivity, specificity and precision for detecting cannabinoids in biological fluids and with lower detection levels than previously possible, due to the availability for the first time of large quantities of highly-pure THC glucuronide GC-MS standards. The use of THC glucuronide GC-MS standard eliminates the imprecision and largely unknown recovery biases inherent in current methodologies, e.g., those using hydrolysis, and this allows the analyst to precisely determine the % recovery in the assay (e.g., as disclosed in Example 22). By calculating the % recovery the analyst can adjust the lower overall detection limits of the analytical procedure downward on a sample-by-sample basis until a suitable level of detection is achieved with an acceptable level of recovery and assay precision (i.e., reproducibility). Thus, the lower-level of sensitivity (i.e., in ng/ml) of the assay protocol can be adjusted on a case-by-case basis, and results reported to the limits of the assay, as allowed by the nature of the biological sample. The lower-level detection sensitivity of the assay may be adjusted downward (i.e., into the range of 0.5 to 5 ng/mL) or upward (i.e., into the range of 50 to 500 ng/mL) based upon a very precise determination of % of recovery of the deuterated THC glucuronide standard, as directly compared with the non-deuterated THC glucuronide standard.

In particular, current methods for analysis of 11-nor-$\Delta^9$ THC-9-carboxylic acid glucuronide in biological samples use 11-nor-$\Delta^9$ THC-9-carboxylic acid as a calibration standard and a trideutero-11-nor-$\Delta^9$ THC-9-carboxylic acid as the internal standard in GC-MS quantization. In the procedure the biological sample is extracted to obtain the THC metabolite, and then the THC metabolite and the standard are both hydrolyzed prior to GC-MS. Both the extraction and hydrolysis are subject to unpredictable errors.

In a presently most preferred embodiment of the invention, undeuterated 11-nor-$\Delta$-THC-9-carboxylic acid glucuronide is used for the calibration standard and deuterated 11-nor-$\Delta^9$-THC-9-carboxylic acid glucuronide is used for the internal standard for calculating percentage recovery. Both are added directly to the biological sample so that a percentage recovery can be calculated that provides a correction factor for individual variations between different biological fluid samples. In this manner varying matrix effects can be quantified and corrected for, i.e., without relying of estimates of questionable and potentially variable hydrolysis and/or extraction efficiencies. A representative example of such a GC-MS assay, and how the data collected in the assay may be used to obtain improved assay precision, specificity and sensitivity, is provided in Example 22, below.

The THC glucuronide compounds, and their derivatives, synthesized by the process of the invention are also useful as analytical standards, calibrating agents, and the like, e.g. in immunoassays and high pressure liquid chromatography (HPLC) assays. In immunoassays the THC glucuronides synthesized by the processes of the invention can be used as calibrators, positive and negative controls, unlabeled ligands, or labeled ligands in assays competitive and non-competitive immunoassays run in a direct or indirect assay format. Representative examples of assays include radioimmunoassays, enzyme-linked immunoassays, fluorescence polarization immunoassays, time resolved fluorescence immunoassays, and the like.

Other embodiments of the invention provide methods for selecting specific immunoglobulin receptors useful in immunoassays, (e.g., antibody, antibody fragments, and antibody proteins prepared by recombinant methods). The specific immunoglobulin receptors of the invention react in a specific manner with a $\Delta^8$- or $\Delta^9$-THC glucuronide but not with the corresponding $\Delta^8$- or $\Delta^9$-THC-carboxylic acid, (i.e., the corresponding $\Delta^8$- or $\Delta^9$-THC carboxylic acid is that THC carboxylic acid which has the same chemical structure as the $\Delta^8$- or $\Delta^9$-THC glucuronide, but lacking the glucuronide group). Methods are routine in the art for evoking immune response in animals to haptens, i.e., THC glucuronides, as well as for, immunochemical purification of immunoglobulin and immunoglobulin fragments, and preparation of labeled immunoglobulin reagents suitable for use in immunoassays. Briefly, preparation of polyclonal immunoglobulin specific to a desired $\Delta^8$- or $\Delta^9$-THC glucuronide is accomplished by immunizing an animal host with the desired $\Delta^8$- or $\Delta^9$-THC glucuronide hapten coupled to a suitable carrier molecule. Specific polyclonal antibody is purified from serum by affinity chromatography on a suitable resin having the bound THC carboxylic acid (i.e., to bind THC carboxylic acid reactive immunoglobulin to the resin) or THC glucuronide (i.e, to bind THC glucuronide reactive immunoglobulin to the resin). Specific monoclonal antibody is prepared by fusing immune spleen cells with cells of a suitable myeloma cell line, followed by selecting hybridoma clones, and then screening for clones of hybridoma cells secreting immunoglobulin receptors that bind to the $\Delta^8$- or $\Delta^9$-THC glucuronide but not to the $\Delta^8$- or $\Delta^9$-THC carboxylic acid. Representative examples of these methods are described in Example 24, below.

Representative immunoglobulin receptors include IgG and IgM, Ig fragments e.g., $F(ab')_2$, Fab', Fab, Fv and the like, as well as genetically-engineered molecules containing complementary determining region (CDR) sequences, i.e., amino acid residues involved in antigen binding by the $F_v$ portion of the molecule. Specific immunoglobulin receptors of the invention may be used in immunoassays, e.g. by immobilizing them on a solid phase, or placing them in a solution, suspension, or mixture with the biological sample being tested. When used in an immunoassay the immunoglobulin receptors of the invention form a specific antigen-antibody complex with a THC glucuronide but not with the corresponding THC carboxylic acid.

Therapeutic Uses of Chemically Synthesized THC Glucuronides

The availability of substantial quantities of highly-purified THC glucuronides, e.g. 11-nor-$\Delta^9$-THC-9-carboxylic acid glucuronide, provides for the first time a ready source of therapeutic compounds for use in testing the effects of THC metabolites on brain and other tissues. THC metabolites are known to have value as clinical therapeutic agents in the treatment of cancer, and other diseases. However, substantial quantities of THC glucuronides have not previously been available, and previous studies have also not been able to accurately determine the levels of THC glucuronides in blood and tissue fluids, making therapeutic dosing problematic. Embodiments of the invention provide production methods for organic synthesis of biologically-active THC glucuronides that are useful as therapeutic agents. Other embodiments of the invention provide specific immunoglobulin receptors, assay calibrators and standards for immunoassays, HPLC assays, and GC-MS assays. Embodiments of the invention, above, provide assays and reagents that are useful for accurately measuring the therapeutic levels of drug achieved in the blood and tissue fluids of patients receiving a clinically-effective dose of a THC glucuronide. Thus, the therapeutic dosage of a THC glucuronide may now be adjusted by those skilled practitioners on a patient-by-patient basis until a clinically-effective dosage of the THC glucuronide is achieved, then the levels in therapeutically levels in blood may be determine for the patient. In this case a clinically-effective dosage refers to a dosage sufficient to induce a clinical effect, e.g. amelioration of pain and/or nausea in a cancer patient during chemotherapy or following radiation therapy.

EXAMPLE I

Figure 3:
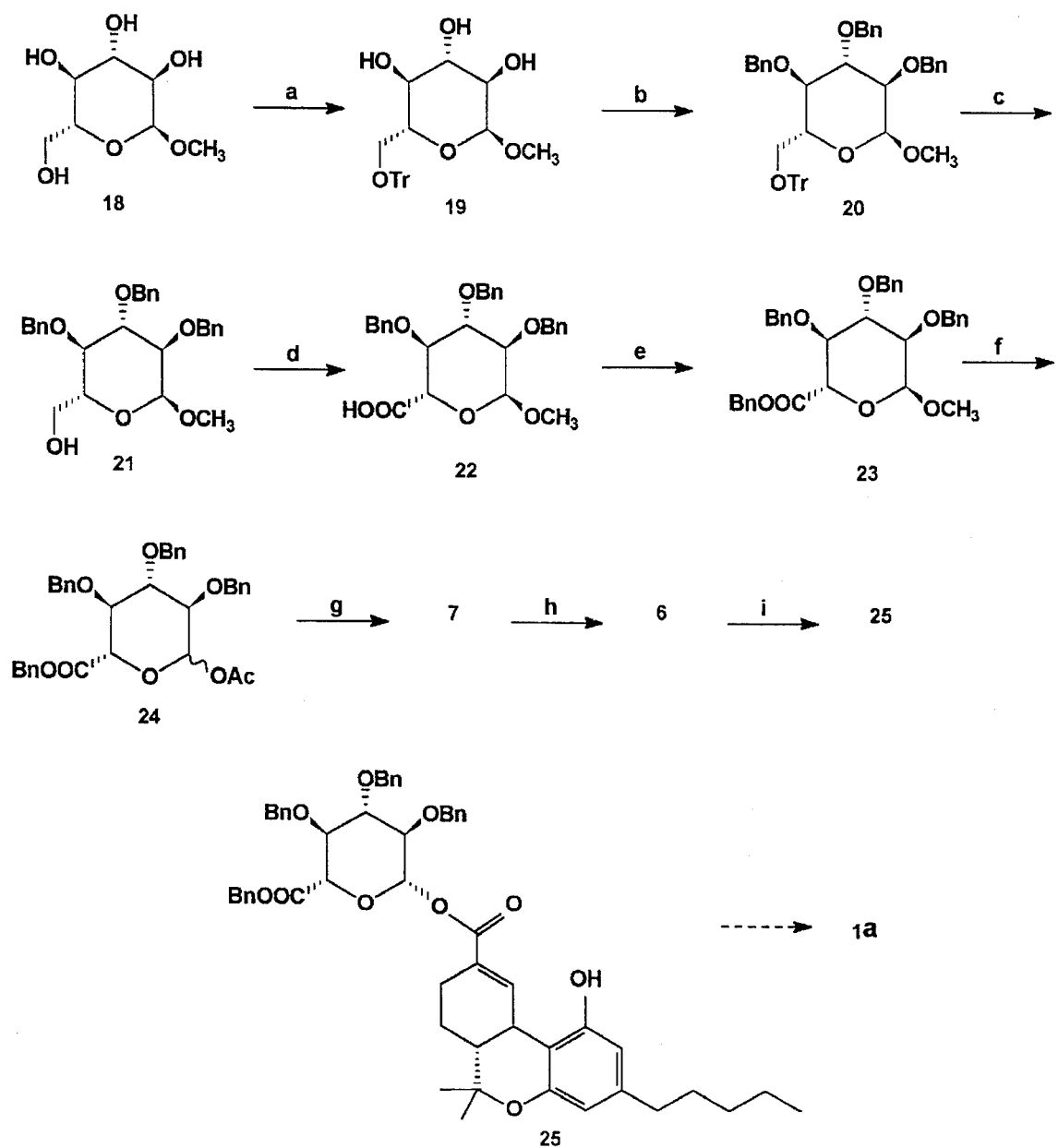
FIG. 3 depicts an instructive example of an abortive Scheme II (as described in Example 1) showing the importance of the proper protective agents for chemical blocking during the synthesis of 11-nor-$\Delta^9$-THC-9-carboxylic acid glucuronide (1) in which removal of the benzyl (Bn) groups on the sugar resulted in destruction of the product. Scheme II proceeds through the steps of "a" to "i", below, involving the following reagents, conditions, and yields: (a) TrCl, Et$_3$N, DMF, 23° C., 48 h, 70%; (b) BnCl, NaH, DMF, 76%; (c) TsOH, CH$_3$OH, 84.4%; (d) CrO$_3$, H$_2$SO$_4$, acetone, 90%; (e) BnOH, DCC, DMAP, DMAP HCl, CHCl$_3$, 77%; (f) Ac$_2$O, AcOH, H$_2$SO$_4$, 16 h, 76%; (g) 2-aminoethanol, DMSO, ethyl acetate, 73%; (h) 5a, DCC, DMAP, DMAP HCl, CHCl$_3$, 73%; (i) n-Bu$_4$NF nH$_2$O, THF, 30%.

Overview: Synthetic Schemes for 11-nor-$\Delta^9$-THC-9-Carboxylic Acid Glucuronide The chemical structures of the intermediates and reagents used for synthesis of 1a are shown as in FIG. 1. Two of the synthetic approaches that were investigated for synthesis of the 11-nor-$\Delta^9$-THC glucuronide target compound are described in detail below, (FIG. 2 and FIG. 3). The key problems of the synthesis of 1a and 1b, in both approaches, were: a) to form the proper β anomeric ester linkage between carboxylic acid 2a and β-D-glucuronic acid, b) to glycosylate the THC carboxylic acid under conditions that do not destroy the THC glucuronide reaction product, c) to select the proper protecting groups that do not interfere with the highly sensitive and labile glucuronide product, d) to de-protect the product without destroying the highly labile glucuronide carboxylic acid ester linkage, and e) to control reaction conditions properly to obtain a reasonable yield of products.

For the first synthetic approach (Scheme I), shown in FIG. 2, the most important advantage was the exclusive formation of the requisite β-isomer. The glucal epoxide 4 was made from the related glucal with dimethyl dioxirane (38). The target compounds, i.e., 1a and its deuterated derivative 1b, were synthesized by this synthesis sequence as described in greater detail, below, and also in Example 2 through Example 9, below.

Chemical synthesis of blocked- THC carboxylic acid intermediate, i.e., TBDMS-blocked-5' deuterated 11-nor-$\Delta^9$-THC-9-carboxylic acid 5b, i.e., for synthesis of the THC glucuronide, was accomplished by the shown in Scheme III, (FIG. 4). Compound 5b was prepared in a stepwise manner similar to that described previously (13), but using deuterated olivetol 26. Further details of this synthesis are described in Example 12 through Example 21, below.

Synthesis of THC glucuronide, is shown in Scheme I (FIG. 2). Triacetylglucal 8 was hydrolyzed into triol 9 with potassium carbonate in methanol and the resulted triol 9 was treated with benzoyl chloride in pyridine to give monobenzoate 10 in 67.8% overall yield. Silylation of 10 with tert-butyldimethylsilyl triflate (TBDMS-triflate) and triethylamine in methylene chloride offered quantitatively bis-silyl benzoate 11. Benzoate 11 was reduced to mono-alcohol 12 with lithium aluminum hydride in 90% yield. Conversion of alcohol 12 to carboxylic acid 14 was effected in two steps: 1) oxidation by Mukaiyama oxidation (39) of alcohol 12 to aldehyde 13, (which could not be purified), and 2) further oxidation of the aldehyde 13 with sodium chlorite. The yield of acid 14 was 34 % for the two steps. Esterification of acid 14 with benzyl alcohol gave 91% yield of benzyl ester 15, which was oxidized to glucal epoxide 4 with dimethyl dioxirane (38). The coupling reaction was carried out in a manner similar to that described previously (38), but importantly, the method was modified to eliminate Lewis acid described as a catalyst (38). Removal of the Lewis acid from the reaction mixture would normally require treatment with a base. However, the product of the reaction is extremely labile, and would undergo either hydrolytic cleavage of the ester, or oxidation, i.e., because the product phenol 3a of the reaction is sensitive to oxidation. The coupling reaction between epoxide 4 and silylated $\Delta^9$-THC acid 5a resulted in 57% yield of coupling compound 3a. The stereochemistry for the coupling reaction was the desired one, i.e., with the $\Delta^9$-THC acid in the equatorial position. This was firmly proven by the strong positive NOE (nuclear Overhauser enhancement) between the axial hemiacetal methine hydrogen and the methine hydrogen adjacent to the carboxylic acid on sugar. Desilylation of coupling compound 3a was effected with aqueous hydrofluoric acid in acetonitrile. The reaction was clean but slow. It offered tetraol 16a in 33% yield with 62% of monosilyl compound 17a recovered even though it was kept stirring for 2 days. Re-treatment of 17a with aqueous hydrofluoric acid under the same condition gave another batch of tetraol 16a and monosilyl 17a. (The reason for the slow reaction may be due to the silyl ether group (i.e., at position 4) next to the benzyl carboxylate (i.e., at position 5) of the glycal sugar moiety.) Removal of the benzyl ester of 16a was smoothly done under hydrogen atmosphere in the presence of Pd catalyst in ethyl acetate to produce the final THC glucuronide compound 1a in quantitative yield. For the final compound 1a, two facts proved the β-glycosidic linkage: 1. With regard to compound 3a, NOE experiments indicated that the hydrogen at $C_1$ and hydrogen at $C_5$ are both axial; 2. The chemical shift of the hydrogen at $C_1$ is γ 5.64 and the coupling constant J is 8.1 Hz which corresponds with values commonly associated with β-linkage compounds (40). The synthesis of the deuterated glucuronide 1b was completed using the same procedure as Scheme I (FIG. 2) but using deuterated $\Delta^9$-THC acid 5b instead of $\Delta^9$-THC acid 5a. The yield of coupling compound 3b was up to 72% and the yield of 16b was up to 47%. (The latter yields were significantly higher than the yield of 3a and 16 a, because of the more carefully optimized reactions).

A second (unsuccessful) approach, Scheme II (FIG. 3), shows important potential pitfalls encountered in the glycosylation method for synthesis of THC glucuronides, namely, a) the problems encountered in obtaining the desired anomeric linkage of the product; b) the problems encountered with when using improper blocking groups to protect the sugar, and/or the improper conditions for removing these blockers from the product of the reaction; and, c) problems of low yield.

In Scheme II (FIG. 3), the intermediate 7, sugar moiety, and the coupling compound 6 were prepared following published procedures (41–43), but with some improvements. Accordingly, α-D-methylglucoside 18 was treated with trityl chloride and triethylamine in DMF to give monotrityl compound 19 in 70% yield. Benzylation of 19 with benzyl chloride and sodium hydride in DMF offered 76% yield of benzyl compound 20 . Treatment of 20 with p-toluenesulfonic acid in methanol produced primary alcohol 21 in 84.4% yield. Conversion of alcohol 21 to carboxylic acid 22 was carried by Jones oxidation in 76% yield. Esterification of acid 22 and benzyl alcohol was performed with DCC and DMAP in chloroform to give benzyl ester 23 in 77% yield. Transformation of methylglucoside to free OH hemiacetal 7 was done in two steps: acetylation of 23 with acetic anhydride in acetic acid in the presence of catalytic sulfuric acid in 76% yield, and hydrolysis of the resulting acetate 24 with 2-aminoethanol in ethyl acetate and dimethylsulfoxide in 73% yield (44).

Coupling reaction of 7 and $\Delta^9$-THC acid 5a (step h, FIG. 3) was completed with DCC, and DMAP in chloroform to give 73% yield of protected glucuronide 6. $^1$H NMR indicated that, unlike the product of Scheme I, above, the reaction product was a mixture of $\alpha$ and $\beta$ isomers in an approximate ratio of 1:2.

In an attempt to de-protect the target compound 1a, treatment of 6 with tetra-n-butylammonium fluoride in THF gave the phenol 25, but with only a 30% yield. The reason for this poor yield for desilylation probably is due to alkalinity of quaternary amine salt and good nucleophilic activity of the reagent.

Debenzylation (i.e., de-blocking) of 25 (FIG. 3) was examined under a hydrogen atmosphere in the presence of Pd catalyst. Unfortunately, the reaction was unsuccessful because a long period of time was required for removal of four benzyl groups and reduction of the double bond took place. The purification of the crude compound was also extremely difficult. Thus, Scheme II (FIG. 3) points out pitfalls of: a) improper choice of blocking agents for protecting the sugar; b) improper methods for de-protecting the product; and, c) poor yield.

EXAMPLE 2

Synthesis of Benzoyl-Protected Tri-O-Sugar: Step a and Step b Scheme I (FIG. 2)

To a solution of tri-O-acetyl-D-glucal 8 (25 g, 92 mmol) in methanol (100 mL) was added potassium carbonate (1.0g). The mixture was stirred overnight at 23° C., TLC indicated no starting material or mono- or di-acetyl intermediates. Most of the solvent was removed on the rotavaporator and the residue was pumped to dryness.

The residue was dissolved in anhydrous pyridine (160 mL) and was cooled in an ice-water bath. To the solution benzoyl chloride (12.8 mL, 110.4 mmol) was dropwise added at 0° C. The reaction was monitored by thin layer chromatography (TLC). If necessary, more benzoyl chloride was added until the triol 9 was converted completely.

The reaction mixture was dissolved in methylene chloride and the solution was washed with water and brine, and dried over anhydrous magnesium sulfate. Concentration and column chromatography were conducted on silica gel with hexane-ether (1:3) to give benzoate 10 (15.6 g) in 67.8% yield. It converted to white crystals while it was stored at 0° C.

Rf: 0.25, hexane-ether (1:4).
$[\alpha]^{23}$d+36.9 (c, 0.00436 g/mL, CHCl$_3$).
IR(neat): 3460, 3200 (b), 2900, 1705, 1640, 1600, 1290, 1120, 710 cm$^{-1}$.
$^1$H NMR(300 MHz, CDCl$_3$); 8.09–7.43 (m, 5 H); 6.35 (dd, J=1.5 Hz, 6.0 Hz, 1 H); 4.94 (dd, J=3.0 Hz, 12.3 Hz, 1 H); 4.76 (dd, J=2.4 Hz, 6.0 Hz, 1 H); 4.50 (dd, J=2.4 Hz, 12.3 Hz, 1 H); 4.35 (d, J=6.0 Hz, 1 H); 4.01 (ddd, J=2.7 Hz, 3.0 Hz, 9.6 Hz, 1 H); 3.59 (ddd, J=2.4 Hz, 9.6 Hz, 12.3 Hz, 2 H).
$^{13}$C NMR(75 MHz, CDCl$_3$); 167.53; 144.20; 133.47; 129.88; 129.27; 128.44; 102.84; 76.43; 69.63; 69.48; 63.19.
MS: 250 (M$^+$), 178 (10%), 122(18%), 105(100%), 97(18%), 77(45%).
Exact mass: Calcd. for C$_{13}$H$_{14}$O$_5$: 250.0841; found: 250.0878.

EXAMPLE 3

Synthesis of Benzoyl-and-TBDMS-Blocked Tri-O-Sugar: Step c Scheme I (FIG. 2)

To a solution of benzoate 10 (12.0 g, 48 mmol) and triethylamine (27.7 mL, 192 mmol) in methylene chloride (300 mL) was added t-butyldimethylsilyltriflate (33.0 mL, 144 mmol) dropwise at 0° C. The reaction mixture was kept stirring for 1 h at that temperature and the reaction was quenched with water.

The organic layer was washed with brine, dried over anhydrous magnesium sulfate and evaporated on the rotavaporator. The residue was purified on a silica gel column with hexane-ether (20:1) to give a quantitative yield of bissilyl compound 11 as a colorless liquid.
Rf: 0.80, hexane-ether (10:1).
$[\alpha]^{23}$d-13.9 (c, 0.0183 g/mL, CHCl$_3$).
IR(neat); 3060, 2950, 2930, 2890, 2860, 1730, 1640, 1270, 1250, 1090, 840, 780 cm$^{-1}$.
$^1$H NMR(300 Mhz, CDCl$_3$); 8.08–7.41 (m, 5 H); 6.36 (d, J=6.3 Hz, 1 H); 4.81–4.77 (m, 1 H); 4.62 (dd, J=7.8 Hz, 12 Hz, 1 H); 4.51 (dd, J=3.3 Hz, 12 Hz, 1 H); 4.32 (m, 1 H); 3.92 (m, 2 H); 0.90(s, 18 H); 0.12(s, 3 H); 011(s, 6 H); 0.10 (s, 3 H)
$^{13}$C NMR(75 MHz, CDCl$_3$); 166.38; 142.73, 132.91, 130.10, 129.63, 128.28, 101.69, 76.59, 70.26, 66.22, 63.15, 25.82, 25.76, 18.04, 17.96, -4.23, -4.34, -4.47, -4.78.
MS: no M$^+$, 463, 421 (11%), 299 (18%), 225 (13%), 179 (66%), 147 (13%), 105 (100%), 81 (10%), 77 (16%), 75 (14%), 73 (54%).
Exact mass: Calcd. for M$^{+-CH}$$_3$, C$_{24}$H$_{39}$O$_5$Si: 463.2336; found: 463.2331.

Next, to a solution of benzoate 11 (660 mg, 1.38 mmol) in ether was added lithium aluminum hydride (LAH; 78 mg, 2.07 mmol) in one portion at 0° C. The reaction mixture was stirred for 6 hours at 0° C. and then the reaction was quenched by carefully adding brine to make LAH a sandy precipitate. The mixture was filtered and the filtration cake was washed with ether. Organic layers were combined and concentrated in a rotavaporator. The residue was chromatographed on a silica gel column with hexane-ether (5:1) to offer the alcohol 12, which became white fine crystals (480 mg), in 93% yield.
Rf: 0.40, hexane-ether (4:1)
$[\alpha]^{23}$$_d$-54.1° (c, 0.0157 g/mL, CHCl$_3$)
IR (neat): 3300 (b), 3060, 2950, 2920, 2880, 2850, 1640, 1460, 1250, 1090, 840, 780 cm$^{-1}$.
$^1$H NMR (300 MHz, CDCl$_3$): 6.39 (d, J=6.3 Hz, 1 H); 4.72 (dd, J=4.8 Hz, 5.7 Hz, 1 H); 4.03 (dd, J=4.8 Hz, 9.6 Hz, 1 H); 3.95 (dd, J=3.3 Hz, 3.6 Hz, 1 H); 3.88 (dd, J=5.7 Hz, 5.7 Hz, 1 H); 3.82 (dd, J=3.3 Hz, 3.6 Hz, 1 H); 3.76 (dd, J=4.8 Hz, 8.4 Hz, 1 H); 3.72 (dd, J=4.8 Hz, 8.4 Hz, 1 H); 2.51 (dd, J=5.7 Hz, 8.4 Hz, 1 H); 0.90 (s, 9 H); 0.89 (s, 9 H); 0.11 (s, 6 H); 010 (s,6 H).
$^{13}$C NMR (75 MHz, CDCl$_3$): 143.54, 101.28, 78.76, 70.52, 66.76, 61.57, 25.79, 25.74, 17.95, -4.33, -4.44, -4.78.
MS: no M$^+$, 317 (4%), 299 (2%), 273 (2%), 245 (3%), 225 (3%), 185 (25%), 147 (28%), 129 (73%), 101 (11%), 75 (100%), 73 (83%).
Exact mass: Calcd. for C$_{14}$H$_{29}$O$_4$Si$_2$ (M$^+$-C$_4$H$_9$): 317.1604; found: 317.1587.

EXAMPLE 4

Synthesis of TBDMS-Blocked Tri-O-Sugar Aldehyde: Step e Scheme I (FIG. 2)

To a suspension of magnesium turnings (360 mg, 15 mmol) in THF (30 mL) was added 2-bromopropane dropwise. The Grignard reagent was stirred for 0.5 hours at 23° C. after the metal was dissolved. A portion of t-butanol (1.68 mL, 18 mmol) was added to the Grignard reagent solution at 0° C. and the mixture was stirred at 0° C. for 15 minutes and at 23° C. for 15 minutes. The t-butoxide solution was transferred to a solution of alcohol 12 (3.74 g, 10 mmol) in THF (15 mL) at 0° C. and then the mixture was stirred at 23° C. for 15 minutes. After that a solution of 1,1'-(azodicarbonyl)dipiperidine (3.28 g, 13 mmol) in THF (25 mL) was added to the previous reaction mixture and the whole became a dark brown solution. The reaction mixture was stirred at 23° C. for 2 days, diluted with hexane-ether (1:1) and filtered through a short silica gel column. The column was washed with hexane-ether (1:1). The filtrate and washes were combined, concentrated to give crude aldehyde 13 (2.90 g). This labile crude aldehyde 13 was applied to next oxidation without purification.

$^1$H NMR(300 MHz, CDCl$_3$); 9.49 (d, J=1.5 Hz, 1 H); 6.53 (d, J=6.3 Hz, 1 H); 4.93 (ddd, J=1.5 Hz, 6.0 Hz, 6.0 Hz, 1 H); 4.05 (m, 1 H).

EXAMPLE 5

Synthesis of TBDMS-Blocked Tri-O-Sugar Carboxylic Acid: Step f Scheme I (FIG. 2)

To a solution of crude aldehyde 13 (4.36 g, 11.7 mmol) in a mixture of t-butanol (120 mL), saturated solution of sodium dihydrophosphate (70 mL) and 2-methyl-2-butene (15 mL) was added sodium chlorite (756 mg, 12 mmol) in small portions under vigorous stirring. The reaction was monitored by TLC and was completed in 6 hours.

The reaction mixture was extracted with ethyl acetate and all extracts were dried and concentrated on rotavaporator. The residue was chromatographed on a silica gel column with hexane-ether (2:1) to offer acid 14 (1.98 g), a colorless liquid, in 34% overall yield.

Rf: 0.35, hexane-ether (2:1).

$[\alpha]^{23}$d-40.0° (c, 0.00638 g/mL, CHCl$_3$).

IR(neat): 3500–2400, 3080, 2960, 2930, 2890, 2860, 1730, 1650, 1460, 1250, 1110, 1070, 890, 840, 780 cm$^{-1}$.

$^1$H NMR(300 MHz, CDCl$_3$): 6.49 (d, J=6.3 Hz, 1 H); 4.85 (ddd, J=1.5 Hz, 6.0 Hz, 6.0 Hz, 1 H); 4.53 (dd, J=1.2 Hz, 2.1 Hz, 1 H); 4.27 (dd, J=2.1 Hz, 4.2 Hz, 1 H); 3.78 (ddd, =1.2 Hz, 2.1 Hz, 5.4 Hz, 1 H); 0.89 (s, 9 H); 0.83 (s, 9 H); 0.13 (s, 3 H); 0.12 (s, 3 H); 0.05 (s, 3 H); 0.04 (s, 3 H).

$^{13}$C NMR(75 MHz, CDCl$_3$); 174.54, 143.22, 101.01, 74.90, 70.15, 63.70, 25.67, 25.55, 18.02, 17.79, −4.44, −4.80, −4.92, −5.01.

MS: no M$^+$, 331 (7%), 199 (15%), 171, 129, 99.

Exact mass: Calcd. for M$^+$-C$_4$H$_9$, C$_{14}$H$_{27}$O$_5$Si$_2$: 331.1397; found: 331.1396.

EXAMPLE 6

Synthesis of Benzyl-TBDMS-Blocked Tri-O-Sugar: Step g Scheme I (FIG. 2)

To a solution of bis-silyl glucal acid 14 (54 mg, 0.14 mmol), benzyl alcohol (76 mg, 0.70 mmol), N,N-dimethylpyridine (52 mg, 0.42 mmol), and N,N-dimethylpyridine hydrochloride (33 mg, 0.21 mmol) in chloroform (1 mL) was added dicyclohexylcarbodiimide (58 mg, 0.28 mmol) in one portion. The reaction mixture was kept stirring for 24 hours at 23° C. and the reaction was monitored by TLC.

The reaction mixture was filtered and the filtrate was concentrated on rotavaporator. The residue was subjected to column chromatography on silica gel with hexane-ether (20:1) to give benzyl ester 15 (61 mg), a colorless liquid, in 91% yield.

Rf: 0.60, hexane ether (10:1).

$[\alpha]^{23}$d-18.4° (c, 0.0110 g/mL, CHCl$_3$).

IR(neat): 3060, 3030, 2950, 2920, 2880, 2850, 1770, 1730, 1650, 1460, 1250, 1180, 1100, 1070, 1000, 990, 840, 780 cm$^{-1}$.

$^1$H NMR(300 MHz, CDCl$_3$); 7.36–7.34(m, 5 H); 6.53 (d, J=6.3 Hz, 1 H); 5.27 (d, J=12.6 Hz, 1 H); 5.03 (d, J=12.6 Hz, 1 H); 4.86 (ddd, J=1.5 Hz, 6.3 Hz, 6.3 Hz, 1 H); 4.59 (dd, J=1.5 Hz, 2.1 Hz, 1 H); 4.30 (dd, J=2.1 Hz, 4.2 Hz, 1 H); 3.82 (ddd, J=1.2 Hz, 2.1 Hz, 5.1 Hz, 1 H); 0.90 (s, 9 H); 0.87 (s, 9 H); 0.13 (s, 3 H); 0.12 (s, 3 H); 0.06 (s, 3 H); 0.05 (s, 3 H).

$^{13}$C NMR(75 MHz, CDCl$_3$): 168.06, 143.45, 135.56, 128.42, 128.08, 127.84, 100.89, 75.40, 70.56, 66.54, 64.14, 25.78, 25.68, 18.11, 18.05, −4.42, −4.71, −4.85.

MS: no M$^+$, 421 (8%), 403 (23%), 285 (6%), 245 (7%), 212(12%), 171 (9%), 147 (14%), 129 (45%), 105 (48%), 91 (100%), 73 (67%).

Exact mass: Calcd. for C$_{21}$H$_{33}$O$_5$Si$_2$ (M$^+$—C$_4$H$_9$): 421.1866; found: 421.1836; calcd. for C$_{21}$H$_{31}$O$_4$Si$_2$ (M$^+$-C$_4$H$_9$-H$_2$O): 403.1761; found: 403.1769.

EXAMPLE 7

Synthesis of Benzyl-TBDMS-Blocked-THC Carboxylic Acid Glucuronide: Step h and Step i Scheme I (FIG. 2)

To a solution of benzyl ester 15 (63 mg, 0.13 mmol) in methylene chloride (4 mL) was dropwise added freshly prepared dimethyl dioxirane solution (38) in acetone at 0°0 C. The reaction was monitored by TLC until no starting material present. Most of solvent was removed with N$_2$ stream and the residue, crude epoxide 4, was pumped for 0.5 hours. The crude epoxide 4 was dissolved in THF (2 mL) and cooled to −78° C. To this chilled solution was added a solution of silylated Δ$^9$-THC-9-carboxylic acid 5a (77 mg, 0.17 mmol) in THF (2 mL). The reaction mixture was stirred at −78° C. for 2 hours and at 0° C. overnight. Most of solvent was removed and the residue was chromatographed on silica gel column with hexane-ether (4:1) to give coupling compound 3a (71 mg) in 57.3% yield as a colorless liquid.

Rf: 0.46, hexane-ether (3:1).

IR(neat): 3500 (b), 3060, 3030, 2950, 2920, 2890, 2860, 1760, 1730, 1615, 1570, 1470, 1425, 1250, 1070, 835,780 cm$^{-1}$.

$^1$H NMR(300 MHz, CDCl$_3$): 7.90 (d, J=1.2 Hz, 1 H); 7.26–7.15 (m, 5 H); 6.28 (d, J=1.5 Hz, 1 H); 6.22 (d, J=1.5 Hz, 1 H); 6.05 (d, J=3.3 Hz, 1 H); 5.15 (d, J=12.6 Hz, 1 H); 5.02 (d, J=12.6 Hz, 1 H); 4.37 (s, 1 H); 3.91 (dd, J=3.0 Hz, 3.3 Hz, 1 H); 3.65 (m, 1 H); 3.28 (d, J=9.6 Hz, 1 H); 3.19 (d, J=10.5 Hz, 1 H); 2.45 (dd, J=7.2 Hz, 7.5 Hz, 1 H); 1.96–1.89 (m, 1 H); 1.60–1.52(m, 4 H); 1.41(s, 3 H); 1.33–1.29(m, 2 H); 1.08(s, 3H); 0.99(s, 9H); 0.90 (s, 18 H); 0.88 (t, J=6.9 Hz, 3 H); 0.30 (s, 3 H); 0.17 (s, 3 H); 0.14(s, 3 H); 0.12 (s, 3 H); 0.11 (s, 3 H); 0.07 (s, 3 H).

$^{13}$C NMR(75 MHz, CDCl$_3$): 168.47, 165.97, 154.55, 154.36, 144.87, 142.75, 135.05, 128.40, 128.09, 127.59, 111.33, 110.62, 110.37, 93.35, 76.68, 75.96, 71.28, 71.18, 70.69, 66.75, 44.37, 35.63, 34.85, 31.46, 30.69, 27.48, 25.95, 25.69, 24.27, 22.55, 18.88, 18.50, 18.25, 17.84, 14.03, −3.63, −4.08, −4.54, −4.67, −4.79, −5.00.

MS: 952.6 (M$^+$), 895.5, 849.5, 787.4, 759.4, 458 (30%), 401 (20%), 373 (33%), 305 (12%), 169 (10%), 129 (25%), 91 (100%), 73 (60%).

EXAMPLE 8

De-blocking of THC Carboxylic Acid Glucuronide: Removal of TBDMS Protector; Step j Scheme I (FIG. 2)

To a solution of coupling compound 3a (38 mg, 0.04 mmol) in acetonitrile (4 mL) was added aqueous hydrofluoric acid (48%, 0.04 mL) at 0° C. The reaction mixture was stirred at that temperature for 2 days. Most of the solvent was removed with $N_2$ stream, and the residue was chromatographed on a silica gel column with $CHCl_3$—$CH_3OH$ (19:1) to give tetraol 16a (8 mg) in 33% yield with monosilyl compound 17a (structure the same as 3 but with a single TBDMS group in either the 15 or 16 position; 18 mg) in 62% yield as colorless liquids.

tetraol 16a:

Rf: 0.13 for tetraol 16a, $CHCl_3$—$CH_3OH$ (19:1).

IR(neat): 3420 (b), 2920, 2870, 1730, 1700, 1620, 1580, 1450, 1420, 1380, 1250, 1200, 1180, 1060, 1040, 900, 840 $cm^{-1}$.

$^1$H NMR(300 MHz, $CD_3COCD_3$): 8.15 (d, J=1.8 Hz, 1 H); 7.43–7.31 (m, 5 H); 6.30 (d, J=1.5 Hz, 1 H); 6.15 (d, J=1.5 Hz, 1 H); 5.65 (d, J=8.0 Hz 1 H); 5.20 (s, 2 H); 4.07 (d, J=9.3 Hz, 1 H); 3.70 (dd, J=9.0 Hz, 9.3 Hz, 1 H); 3.58 (dd, J=8.7 Hz, 9.0 Hz, 1 Hz); 3.46 (dd, J=8.0 Hz, 8.7 Hz, 1 H); 3.36 (d, J=10.8 Hz, 1 H); 2.59–2.51 (m, 1 H); 2.42 (dd, J=7.5 Hz, 7.7 Hz, 2 H); 1.70–1.44 (m, 4 H); 1.40 (s, 3 H); 1.35–1.25 (m, 4 H); 1.08 (s, 3 H); 0.87 (t, J=6.9 Hz, 3 H).

$^{13}$C NMR(75 MHz, $CD_3COCD_3$); 168.91, 165.93, 156.45, 155.65, 145.40, 143.52, 136.67, 129.11, 128.85, 128.75, 109.67, 108.07, 95.07, 77.28, 76.96, 73.37, 72.53, 67.08, 45.31, 36.02, 35.29, 32.05, 31.48, 27.65, 25.85, 24.68, 23.01, 19.10, 14.13.

MS: No $M^+$, 434 (6%), 419 (8%), 344 (29%), 329 (47%), 299(38%), 283 (18%), 91 (100%).

Exact mass: Calcd. for $C_{34}H_{38}O_8$: 574.2567; found: 574.2537.

EXAMPLE 9

De-blocking of THC Carboxylic Acid Glucuronide: Removal of Benzyl Protector; Step k Scheme I (FIG. 2)

A solution of tetraol 16a (22 mg, 0.036 mmol) in ethyl acetate (8 mL) was vigorously stirred in the presence of palladium catalyst (5 mg, 10% on carbon, Lancaster) under $H_2$ atmosphere at 23° C. The reaction was monitored by TLC and was completed in 0.5 hours. The catalyst precipitate was filtered off and the filtrate was concentrated to give a colorless liquid, glucuronide 1a (18 mg) in 96% yield.

Rf: 0.16, $CHCl_3$—$CH_3OH$ (2:1).

IR(neat); 3700–2400, 2920, 2850, 2340, 2220, 1725, 1710, 1620, 1575, 1420, 1380, 1240, 1180, 1060, 920, 830 $cm^{-1}$.

$^1$H NMR(300 MHz, $CD_3COCD_3$): 8.15 (d, J=1.8 Hz, 1 H); 6.29 (d, J=0.9 Hz, 1 H); 6.15 (d, J=0.9 Hz, 1 H); 5.64 (d, J=8.1 Hz, 1 H); 3.99(d, J=9.3 Hz, 1 H); 3.66 (dd, J=9.0 Hz, 9.3 Hz, 1 H); 3.57 (dd, J=8.7 Hz, 9.0 Hz, 1 H); 3.46 (dd, J=8.1 Hz, 8.7 Hz, 1 H); 3.36 (d, J=10.2 Hz, 1 H); 2.60–2.52 (m, 1 H); 2.42 (dd, J=7.5 Hz, 7.8 Hz, 2 H); 1.65–1.42(m, 2 H); 1.40(s, 3 H); 1.31(m, 6 H); 108(s, 3 H); 0.87 (t, J=6.9 Hz, 3 H).

$^{13}$C NMR (125 MHz, $CD_3COCD_3$): 170.06, 166.14, 156.51, 155.78, 145.48, 143.63, 129.09, 109.82, 108.21, 107.66, 95.18, 77.37, 77.14, 76.46, 73.42, 72.49, 45.53, 36.12, 35.47, 32.14, 31.44, 27.77, 25.94, 24.83, 23.04, 19.21, 14.13.

EXAMPLE 10

Synthesis of 5'Tri-deuterated Benzyl-TBDMS-Blocked THC Carboxylic Acid Glucuronide; Step h and Step i Scheme I (FIG. 2)

To a solution of benzyl ester 15 (96 mg, 0.20 mmol) in methylene chloride (6 mL) was dropwise added freshly prepared dimethyl oxirane solution in acetone at 0° C. The reaction was monitored by TLC until no starting material was present. Most of the solvent was removed with $N_2$ stream and the residue, crude epoxide 4, was pumped for 0.5 hours. The crude epoxide 4 was dissolved in THF (4 mL) and cooled to –78° C. To this chilled solution was added a solution of TBDMS protected $\Delta^9$-THC-9-carboxylic acid-$d_3$ (110 mg, 0.24 mmol) 5b in THF (4 mL). The reaction mixture was stirred at –78° C. for 2 hours and at 0° C. overnight. Most of solvent was removed and the residue was chromatographed on silica gel column with hexane-ether (4:1) to give deuterated coupling compound 3b (138 mg) in 72.3% yield with recovery of $\Delta^9$-THC-9-carboxylic acid-$d_3$ (27 mg).

Rf: 0.46, hexane-ether (93:1).

$[\alpha]^{23}d$-73.9° (c, 0.00633 g/mL, $CDCl_3$).

IR(neat): 3500 (b), 3070, 3040, 2960, 2930, 2900, 2860, 2220, 2080, 1760, 1730, 1640, 1620, 1570, 1460, 1430, 1260, 1100, 840, 780 $cm^{-1}$.

$^1$H NMR (300 MHz, $CDCl_3$): 7.91 (s, 1 H)7.26–7.17 (m, 5 H); 6.29 (s, 1 H); 6.23 (s, 1 H); 6.05 (d, J=3.3 Hz, 1 H); 5.15 (d, J=12.6 Hz, 1 H); 5.02 (d, J=12.6 Hz, 1 H); 4.37(s, 2 H); 3.91(m, 1 H); 3.66(s, 1 H); 3.20(d, J=10.8 Hz, 1 H); 2.56–2.38 (m, 2 H); 2.46 (dd, J=6.9 Hz 7.4 Hz, 2 H); 1.96–1.90 (m, 1 H); 1.61–1.54 (m, 3 H); 1.41 (s, 3 H); 1.30 (m, 4 H); 1.08 (s, 3 H), 0.99 (s, 9 H); 0.90 (s, 18 H); 0.30 (s, 3 H); 0.18 (s, 3 H); 0.15(s, 3 H); 0.12 (s, 3 H); 0.11 (s, 3 H); 0.08 (s, 3 H).

$^{13}$C NMR(75 MHz, $CDCl_3$): 168.45, 165.97, 154.54, 154.35, 144.86, 142.74, 135.04, 128.40, 128.08, 127.58, 111.32, 110.60, 110.36, 93.34, 76.67, 75.96, 71.30, 71.18, 70.69, 66.75, 44.36, 35.62, 34.84, 31.37, 30.70, 27.48, 25.94, 25.68, 24.25, 22.26, 18.86, 18.48, 18.25, 17.83, –3.64, –4.09, –4.55, –4.68, –4.79, –5.02.

MS: 956 ($M^+$, t), 899 (t), 790 (t), 762 (t), 634 (t), 575 (t), 552(t), 518 (t), 461 (12%), 444, 416, 404, 376 (11%), 358, 336, 305, 129 (13%), 91 (100%).

Exact mass: Calcd. for $C_{52}H_{81}D_3O_{10}Si_3$: 955.5561; found: 955.5635.

EXAMPLE 11

De-blocking of 5'Tri-deuterated THC Carboxylic Acid Glucuronide: Removal of TBDMS Protector; Step j and Step k Scheme I (FIG. 2)

A solution of coupled compound 3b (100 mm, 0.10 mmol) and aqueous hydrofluoric acid (0.10 mL, 48%) in acetonitrile (3 mL) was stirred at 0° C. for 3 days. Most of solvent was removed with $N_2$ stream. The residue was chromatographed on silica gel column with $CHCl_3$-$CH_3OH$ (19:1) to offer tetraol 16b (30 mg) in 46.7% yield and monosilyl compound 17b (36 mg) in 49.5% yield as colorless liquids.

Tetraol 16b:

Rf: 0.22, $CHCl_3$—$CH_3OH$ (19:1).

IR(neat): 3420 (b), 3060, 3030, 2980, 2930, 2860, 2350, 2220, 2070, 1730, 1700, 1620, 1580, 1450, 1430, 1380, 1250, 1200, 1180, 1065, 840 $cm^{-1}$.

1H NMR(300 MHz, $CD_3COCD_3$): 8.15 (d, J=1.8 Hz, 1 H); 7.43–7.30 (m, 5 H); 6.30 (d, J=1.2 Hz, 1 H); 6.15 (d, J=1.2 Hz, 1 H); 5.65 (d, J=8.1 Hz, 1 H); 5.20 (s, 2 H); 4.07 (d,

J=9.3 Hz, 1 H); 3.70 (dd, J=9.0 Hz, 9.3 Hz, 1 H); 3.58 (dd, J=8.7 Hz, 9.0 Hz, 1 H); 3.46 (dd, J=8.1 Hz, 8.7 Hz, 1 H); 3.36 (d, J=10.8 Hz, 1 H); 2.62–2.51 (m, 1 H); 2.42 (dd, J=7.5 Hz, 7.8 Hz, 2 H); 1.66 (ddd, J=1.2 Hz, 12.3 Hz, 12.3 Hz, 2 H); 1.57–1.44 (m, 2 H); 1.40 (s, 3 H), 1.29 (m, 4 H); 1.08 (s, 3 H).

$^{13}$C NMR(75 MHz, CD$_3$COCD$_3$): 169.06, 166.08, 156.57, 155.76, 145.54, 143.63, 136.79, 129.23, 128.97, 128.87, 109.77, 108.19, 95.19, 77.40, 77.07, 73.46, 72.63, 67.21, 45.42, 36.14, 35.41, 32.09, 31.62, 27.78, 25.97, 24.79, 22.87, 19.24.

MS: no M$^+$, 472, 437, 422 (6%), 347 (22%), 332(100%), 302(25%), 286(24%), 108 (11%), 91 (56%).

Exact mass: Calcd. for C$_{34}$H$_{35}$D$_3$O$_8$ (M$^+$–2H$_2$O): 577.2755; found: 577.2751.

Debenzylation of tetraol 16b was accomplished in a manner identical to that described above in Example 9 to yield the target 5' tri-deuterated compound 16.

EXAMPLE 12

Synthesis of 5'Tri-deuterated TBDMS-Blocked THC Carboxylic Acid: Synthesis of Alkylated Acetoacetate 28 Intermediate; Step a Scheme III (FIG. 4A)

To a suspension of sodium hydride (490 mg, 74% in oil, 15 mmol) in THF (30 mL) was dropwise added ethyl acetoacetate (1.95 g, 15 mmol) at 0° C. The mixture was stirred at 23° C. for 0.5 hours after all of the sodium hydride was dissolved. A solution of n-butyl lithium in hexane (5.6 mL, 2.5M, 14 mmol) was added to the sodium salt solution at 0° C. and stirred for another 0.5 hours. To this dianion solution was added a solution of 3,5-dimethoxybenzyl bromide 27 (2.31 g, 10 mmol) in THF (10 mL) at 0° C.

The reaction mixture was stirred for 2 hours, and the reaction was quenched with HCl (1N) and was adjusted to pH 3–4 at 0° C. Aqueous layer was extracted with ether. All organic layers were combined, washed with sodium bicarbonate solution, water, and the organic layer was dried over anhydrous magnesium sulfate. (Concentration and chromatography were conducted on a silica gel column with hexane-ether (3:1) which gave alkylated acetoacetate 28 (2.11 g) as a colorless liquid in 75% yield.)

Rf: 0.28, hexane-ether (2:1).

IR(neat): 2960, 2940, 2840, 1750, 1715, 1600, 1470, 1430, 1370, 1315, 1210, 1160, 1070, 840 cm$^{-1}$.

$^1$H NMR(300 MHz, CDCl$_3$): 6.33–6.30 (m, 3 H); 4.18 (q, J=7.2 Hz, 2 H); 3.77 (s, 6 H); 3.42 (s, 2 H); 2.86 (s, 4 H), 1.26 (t, J=7.2 Hz, 3 H).

$^{13}$C NMR(75 MHz, CDCl$_3$): 201.74, 166.93, 160.69, 142.77, 106.15, 97.93, 61.19, 55.04, 49.20, 44.09, 29.52, 13.89.

MS: 280 (M$^+$, 12%), 235 (3%), 206 (4%), 193 (5%), 178 (9%), 165 (100%), 151 (13%), 135 (6%), 105 (9%).

Exact mass: Calcd. for C$_{15}$H$_{20}$O$_5$: 280.1311; found: 280.1317.

EXAMPLE 13

Synthesis of 5'Tri-deuterated TBDMS-Blocked THC Carboxylic Acid: Synthesis of Deuterated Acetoacetate 29 Intermediate; Step b Scheme III (FIG. 4A)

To a suspension of sodium hydride (876 mg, 74% in oil, 27 mmol) in THF (100 mL) was dropwise added a solution of acetoacetate 28 (8.40 g, 30 mmol) in THF (20 mL) at 0° C. The reaction mixture was stirred for 0.5 hour at 23° C. after all sodium hydride was dissolved, and iodomethane-d$_3$ (1.90 mL, 30 mmol, 99.5% d$_3$, MSD ISOTOPES) was added at 0° C. The reaction mixture was stirred overnight.

The reaction was quenched with HCl (1N) and was adjusted to pH 2–3. The aqueous layer was extracted with ether and all organic layers were combined, washed with water, sodium bicarbonate solution, and brine, and the organic layers were then dried over anhydrous magnesium sulfate. Concentration and chromatography were accomplished on a silica gel column with hexane-ether (3:1) to give deuterated acetoacetate 29, as a colorless liquid, (7.02 g) in 78.7% yield.

Rf: 0.35, hexane-ether (2:1).

IR(neat): 2990, 2980, 2940, 2900, 2840, 2360, 2240, 2120, 2080, 1745, 1715, 1600, 1460, 1200, 1150, 1070, 840 cm$^{-1}$.

$^1$H NMR(300 MHz, CDCl$_3$): 6.33–6.30 (m, 3 H); 4.15 (q, J=7.2 Hz, 2 H); 3.77 (s, 6 H); 3.47 (s, 1 H); 2.96–2.76 (m, 4 H); 1.24 (t, J=7.2 Hz, 3 H).

$^{13}$C NMR(75 MHz CDCl$_3$): 204.79, 170.27, 160.70, 143.02, 106.19, 97.89, 61.18, 55.04, 52.61, 42.64, 29.69, 13.87.

MS: 297 (M$^+$, 12%), 279 (2%), 252 (3%), 205 (3%), 193 (9%), 165 (100%), 151 (26%), 105 (9%).

Exact mass: Calcd. for C$_{16}$H$_{19}$D$_3$O$_5$: 297.1655; found: 297.1652.

EXAMPLE 14

Synthesis of 5'Tri-deuterated TBDMS-Blocked THC Carboxylic Acid: Synthesis of Ketone 30 Intermediate; Step c Scheme III (FIG. 4A)

A solution of keto ester 29 (34.0 g, 0.117 mmol) in ethanol (350 mL, 95%) and sodium hydroxide solution (350 mL, 1N) was gently refluxed for 6 hours. The reaction mixture was cooled to room temperature and extracted with methylene chloride. All organic layers were combined, washed with water and dilute hydrochloric acid (1N) and dried over anhydrous magnesium sulfate. Concentration of the organic layers on a rotavaporator and chromatography on silica gel with hexane-ether (3: 1) produced ketone 30 (24.7 g) as a colorless liquid in 94% yield.

Rf: 0.37, hexane-ether (2:1).

IR(neat): 3000, 2940, 2840, 2220, 2120, 2080, 1720, 1600, 1460, 1440, 1210, 1150, 1070, 840 cm$^{-1}$. $^1$H NMR(300 MHz, CDCl$_3$): 6.30 (d, J=2.1 Hz, 2 H); 6.26 (d, J=2.1 Hz, 1 H); 3.72 (s, 6 H); 2.82–2.77 (m, 2 H); 2.70–2.64 (m, 2 H); 2.35 (s, 2 H).

$^{13}$C NMR(75 MHz, CDCl$_3$): 210.26, 160.59, 143.35, 106.05, 97.69, 54.91, 43.39, 35.56, 29.85.

MS: 225 (M$^+$, 16%), 165 (100%), 151 (15%), 105 (7%), 91 (5%).

Exact mass: Calcd. for C$_{13}$H$_{15}$D$_3$O$_3$: 225.1444 found: 225.1443.

EXAMPLE 15

Synthesis of 5'Tri-deuterated TBDMS-Blocked THC Carboxylic Acid: Synthesis of Bismethylolivetol 31 Intermediate; Step d Scheme III (FIG. 4A)

To a stirred solution of ketone 30 (8.0 g, 35.5 mmol) in ethanol (25 mL, 95%) was added tosylhydrazine (7.92 g, 42.6 mmol). The reaction mixture was heated to reflux gently for 2 hours. Most of the solvent was removed on a rotavaporator and the residue was dissolved in methanol (120 mL). To that solution, sodium borohydride was carefully added in small portions. After addition, the mixture was heated to gently reflux for 4 hours. After cooling, most of solvent was removed and the residue was dissolved in water. The aqueous solution was extracted with ether. All extracts were combined, washed with brine, dried over anhydrous magnesium sulfate. Concentration on a rotavaporator and chromatography on a silica gel column with hexane-ether (10:1) gave bismethylolivetol 31 (5.14 g) in 68.6% yield.

Rf: 0.78, hexane-ether (2:1).

IR(neat): 3000, 2930, 2860, 2840, 2220, 2120, 2080, 1600, 1470, 1430, 1210, 1160, 1060, 830 cm$^{-1}$.

$^1$H NMR(300 MHz, CDCl$_3$): 6.34 (d, J=1.8 Hz, 2 H); 6.30 (d, J=1.8 Hz, 1 H); 3.78 (s, 6 H); 2.55 (t, J=7.8 Hz, 2 H); 1.63–1.58 (m, 2 H); 1.31–1.27 (m, 4 H).

$^{13}$C NMR(75 MHz, CDCl$_3$): 160.63, 145.42, 106.45, 97.51, 55.22, 36.28, 31.44, 30.98, 22.28.

MS: 211 (M$^+$, 21%), 169 (7%), 153(12%), 152 (100%), 151 (12%), 91 (6%), 77 (6%).

Exact mass: Calcd. for C$_{13}$H$_{17}$D$_3$O$_2$: 211.1652; found: 211.1626.

EXAMPLE 16

Synthesis of 5'Tri-deuterated TBDMS-Blocked THC Carboxylic Acid: Synthesis of Tri-deuterated Olivetol 26 Intermediate; Step e Scheme III (FIG. 4A)

To a solution of bismethylolivetol 31 (4.0 g, 19.0 mmol) was added dropwise a solution of boron tribromide (32 mL, 1M, 32 mmol) in methylene chloride at −78° C. After addition, the reaction mixture was stirred at −78° C. for 1 hour, then at 0° C. for 2 hours, and then at 23° C. overnight. The reaction was quenched with water at 0° C. The organic layer was washed with water, dried over anhydrous magnesium sulfate, and concentrated on a rotavaporator. Chromatography of the dried material on a silica gel column with hexane-ether (3:1) offered olivetol-d$_3$ 26 (3.34 g), in 96% yield.

Rf: 0.12, hexane-ether (2:1).

IR(neat): 3320 (b), 2920, 2860, 2220, 2120, 2080, 1600, 1470, 1150, 1000, 840 cm$^{-1}$.

$^1$H NMR(300 MHz, CDCl$_3$): 6.26 (d, J=2.1 Hz, 2 H); 6.18 (d, J=2.1 Hz, 1 H); 2.45 (t, J=7.8 Hz, 2 H); 1.56–1.51 (m, 2 H); 1.28–1.26 (m, 4 H).

$^{13}$C NMR(300 MHz, CDCl$_3$): 156.25, 146.33, 108.21, 100.22, 35.75, 31.35, 30.69, 22.21.

MS: 183 (M$^+$, 57%), 141 (16%), 137 (20%), 125 (25%), 124(100%), 123 (59%), 95 (7%), 77 (10%), 69 (22%).

Exact mass: Calcd. for C$_{11}$H$_{13}$D$_3$O$_2$: 183.1339; found: 183.1337.

EXAMPLE 17

Synthesis of 5'Tri-deuterated TBDMS-Blocked THC Carboxylic Acid: Synthesis of Cyclization Compound 32 Intermediate; Step f Scheme III (FIG. 4B)

To a solution of olivetol-d$_3$ 26 (610 mg, 3.33 mmol) and n-mentha-7-acetoxy-2,8,-diene-1-ol (13; 700 mg, 3.33 mmol) in methylene chloride (20 mL) was added anhydrous magnesium sulfate (432 mg) and boron trifluoride etherate (0.10 mL) at 0° C. The reaction mixture was stirred at 0° C. for 2 hours and at 23° C. for 12 hours with TLC monitoring and comparison with THC carboxylic acid standards. A portion of sodium bicarbonate (886 mg) was added to the reaction mixture and stirring was continued 0.5 hour.

The reaction mixture was filtered and the filtrate was concentrated to give a light brown residue. The residue was chromatographed on a silica gel column with hexane-ether (5:1) to give the cyclization compound 32 (405 mg) as a light brown liquid in 32.4% yield.

Rf: 0.60, hexane-ether (1:1).

[α]$^{23}$d-120.9° (c, 0.007975 g/mL, CHCl$_3$).

IR(neat): 3420 (b), 3080, 2980, 2920, 2860, 2220, 2120, 2070, 1740, 1710, 1620, 1580, 1430, 1385, 1240, 1180, 1130, 1050, 1020, 960, 840 cm$^{-1}$.

$^1$H NMR(300 MHz, CDCl$_3$): 6.78 (s, 1 H); 6.26 (d, J=0.9 Hz, 1 H); 6.13 (d, J=0.9 Hz, 1 H); 4.49 (s, 2 H); 3.27 (d, J=10.8 Hz, 1 H); 2.42 (dd, J=7.2 Hz, 7.6 Hz, 2 H); 2.30–2.20 (m, 2 H); 2.07 (s, 3 H); 2.00–1.94 (m, 1 H); 1.72 (ddd, J=1.5 Hz, 12.3 Hz, 11.1 Hz, 2 H); 1.60–1.45 (m, 2 H); 1.42 (s, 3 H); 1.28 (m, 4 H); 1.10 (s, 3 ).

$^{13}$C NMR(75 MHz, CDCl$_3$): 171.29, 154.76, 154.29, 142.98, 132.20, 129.81, 109.94, 108.02, 107.52, 68.86, 45.25, 35.45, 33.68, 31.40, 30.63, 27.54, 27.07, 24.46, 22.24, 21.01, 19.23.

MS: 375 (M$^+$, 67%), 316 (26%), 315 (100%), 300(48%), 272 (59%), 247 (14%), 220 (6%), 196 (9%), 165 (5%), 147 (5%), 107 (6%), 91 (11%).

Exact mass: Calcd. for C$_{23}$H$_{29}$D$_3$O$_4$ (M$^+$): 375.2489; found: 375.2472.

EXAMPLE 18

Synthesis of 5'Tri-deuterated TBDMS-Blocked THC Carboxylic Acid: Synthesis of Acetyl-Silyl Compound 33 Intermediate; Step g Scheme III (FIG. 4B)

To a solution of cyclization compound 32 (2.40 g, 6.40 mmol) and imidazole (1.31 g, 19.2 mmol) in N,N-dimethylformamide (15 mL) was added t-butyldimethylsilyl chloride (TBDMS-Cl;1.54 g, 10.2 mmol) in one portion. The reaction mixture was stirred at 23° C. overnight, then diluted with hexane-ether (2:1), and washed with brine. The organic layer was dried over anhydrous magnesium sulfate, concentrated on a rotavaporator to a residue. The residue was chromatographed on a silica gel column with hexane-ether (6:1) to offer acetylsilyl compound 33 (2.76 g), a colorless liquid, in 88.2% yield.

Rf: 0.65, hexane-ether (2:1).

[α]$^{23}$d-114.2° (c, 0.00635 g/mL, CHCl$_3$).

IR(neat): 3060, 2920, 2860, 2220, 2120, 2060, 1740, 1610, 1570, 1420, 1380, 1250, 1220, 1180, 1110, 1060, 840 cm$^{-1}$.

$^1$H NMR(300 MHz, CDCl$_3$): 6.71 (s, 1 H); 6.29 (d, J=0.9 Hz, 1 H); 6.20 (d, J=0.9 Hz, 1 H); 4.48 (d, J=12.3 Hz, 1 H); 4.41 (d, J=12.3 Hz, 1 H); 3.16 (d, J=10.5 Hz, 1 H); 2.44 (dd, J=6.9 Hz, 7.5 Hz, 2 H); 2.25–2.22 (m, 2 H); 2.05 (s, 3 H); 2.00–1.92 (m, 1 H); 1.75–1.65 (m, 2 H); 1.58–1.53 (m, 2 H); 1.41(s, 3 H); 1.30–1.27 (m, 4 H); 1.08 (s, 3 H); 0.99 (s, 9 H); 0.26 (s, 3 H); 0.15 (s, 3 H).

$^{13}$C NMR(75 MHz, CDCl$_3$): 171.00, 154.54, 154.27, 142.46, 131.43, 130.48, 111.96, 111.50, 110.53, 76.75, 68.49, 45.40, 35.56, 33.96, 31.31, 30.66, 27.46, 27.05, 25.90, 24.53, 22.25, 20.96, 19.03, 18.22, −3.65, −4.25.

MS: 489 (M$^+$, 17%), 432 (19%), 431 (16%), 430 (48%), 429 (100%), 416 (20%), 415 (23%), 414 (58%), 413 (16%), 412 (44%), 373(23%), 372 (70%), 330 (9%), 252 (6%), 117 (28%), 95 (28%), 73 (73%).

Exact mass: Calcd. for C$_{29}$H$_{43}$D$_3$O$_4$Si: 489.3354; found: 489.3338.

EXAMPLE 19

Synthesis of 5'-Tri-deuterated TBDMS-Blocked THC Carboxylic Acid: Removal of the Acetyl to Generate Alcohol 34 Intermediate; Step h Scheme III (FIG. 4B)

To a solution of silyl compound 33 (2.06 g, 4.2 mmol) in ether (100 mL) was added lithium aluminum hydride (160 mg, 4.2 mmol) in small portions at 0° C. The reaction mixture was stirred at 0° C. for 1 hour and at 23° C. for 4 hours. The reaction was carefully quenched with water to make lithium aluminum hydride precipitate as a sandy precipitate.

The reaction mixture was filtered and the filtrate cake was washed with ether. All organic solutions were combined and concentrated on a rotavaporator. The resulting residue was chromatographed on a silica gel column with hexane-ether (2:1) to offer a colorless liquid, alcohol 34 (1.67 g), in 90% yield.

Rf: 0.23, hexane-ether (2:1).

$[\alpha]^{23}d$-123.95° (c, 0.0215 g/mL, CHCl$_3$).

IR(neat); 3320 (b), 3060, 2920, 2850, 2210, 2110, 2060, 1610, 1570, 1420, 1380, 1250, 1180, 1110, 1060, 1000, 910, 840 cm$^{-1}$.

$^1$H NMR(300 MHz, CDCl$_3$): 6.66 (s, 1 H); 6.30 (d, J=0.9 Hz, 1 H); 6.21 (d, J=0.9Hz, 1 H); 4.00 (s, 2 H); 3.16 (d, J=10.8 Hz, 1 H); 2.44 (dd, J=6.6 Hz, 7.5 Hz, 2 H); 2.30–2.28 (m, 2 H); 2.00–1.94 (m, 1 H); 1.72–1.63 (m, 1 H); 1.58–1.53 (m, 2 H); 1.41 (s, 3 H); 1.30–1.29 (m, 4 H); 1.09(s, 3 H); 1.00 (s, 9 H); 0.27 (s, 3 H); 0.16 (s, 3 H).

$^{13}$C NMR(75 MHz, CDCl$_3$): 154.55, 154.28, 142.40, 136.44, 127.74, 112.22, 111.49, 110.54, 76.81, 67.56, 45.75, 35.55, 33.88, 31.36, 30.66, 27.49, 26.73, 25.90, 24.65, 22.25, 19.07, 18.23, –3.62, –4.23.

MS: 447 (M$^+$, 20%), 429 (10%), 416 (100%), 390 (9%), 73 (34%).

Exact mass: Calcd. for C$_{27}$H$_{41}$D$_3$O$_3$Si: 447.3248; found: 447.3230.

EXAMPLE 20

Synthesis of 5' Tri-deuterated TBDMS-Blocked THC Carboxylic Acid: Conversion of the Alcohol 34 to the Aldehyde 35 Intermediate; Step i Scheme III (FIG. 4B)

To a suspension of magnesium turnings (130 mg, 5.4 mmol) in THF (11 mL) was added 2-bromopropane (0.50 mL, 5.4 mmol) dropwise. After the metal was dissolved, the mixture was stirred for 0.5 hour at 23° C. To the Grignard reagent t-butanol (0.54 mL) was added at 0° C., and stirring was then continued for 15 minutes at 23° C. This t-butoxide solution was transferred to a solution of alcohol 34 (1.60 g, 3.60 mmol) in THF (8 mL) at 0° C. To this reaction mixture a solution of 1,1'-(azodicarbonyl)dipiperidine (1.71 g, 4.32 mmol) in THF (8 mL) was added at 23° C. The whole reaction mixture became a dark brown solution. The reaction was monitored by TLC by monitoring for disappearance of the starting material and appearance of the product at R$_f$=0.85 in hexane-ether (1:1), and was completed in 2 hours. The reaction was quenched with 2-propanol (0.20 mL) and the reaction mixture was diluted with hexane-ether (1:1). The mixture was washed with brine, dried over anhydrous magnesium sulfate. Concentration and chromatography on a silica gel column with hexane-ether (3:1) gave aldehyde 35 as a colorless liquid (1.47 g) in 92% yield.

Rf: 0.85, hexane-ether (1:1).

$[\alpha]^{23}d$-136.4°(c, 0.00986 g/mL, CHCl$_3$).

IR(neat): 3060, 2920, 2860, 2800, 2700, 2220, 2120, 2060, 1690, 1610, 1570, 1430, 1380, 1260, 1190, 1180, 1110, 1060, 840 cm$^{-1}$.

$^1$HNMR(300 MHz, CDCl$_3$): 9.45 (s, 1 H); 7.79 (d, J=1.5 Hz, 1 H); 6.33 (d, 1.2 Hz, 1 H); 6.25 (d, 1.2 Hz, 1 H); 3.37 (d, J=10.8 Hz, 1 H); 2.56–2.38 (m, 2 H); 2.46 (dd, J=6.9 Hz, 7.5 Hz, 2 H); 2.08–2.01 (m, 1 H); 1.72 (ddd, J=1.8 Hz, 12.6 Hz, 11.1 Hz, 1 H); 1.59–1.54 (m, 2 H); 1.44 (s, 3 H); 1.30 (m, 4 H); 1.12 (s, 3 H); 0.99 (s, 9 H); 0.30 (s, 3 H); 0.17 (s, 3 H).

$^{13}$C NMR(75 MHz, CDCl$_3$): 194.47, 154.99, 154.66, 154.12, 143.23, 139.89, 111.47, 110.83, 109.91, 76.89, 44.94, 35.59, 31.35, 30.66, 27.47, 25.91, 23.70, 22.30, 22.26, 18.94, 18.24, –3.54, –4.20.

MS; 445 (M$^+$, 100%), 416 (71%), 388 (37%), 268 (8%), 73 (52%)

Exact mass: Calcd. for C$_{27}$H$_{39}$D$_3$O$_3$Si: 445.3092; found: 445.3007.

EXAMPLE 21

Synthesis of 5' Tri-deuterated TBDMS-Blocked THC Carboxylic Acid: Conversion of Aldehyde 35 to Carboxylic Acid 5b Product; Step j Scheme III (FIG. 4B)

To a solution of aldehyde 35 (1.47 g, 3.37 mmol) in a solution of t-butanol (60 mL), saturated solution of sodium dihydrogen phosphate (35 mL) and 2-methyl-2-butene (8 mL), was added sodium chlorite (600 mg, 6.66 mmol) in small portions with vigorous stirring. The reaction was monitored by TLC (as above) and was completed in 4 hours. The reaction mixture was extracted with ethyl acetate, and the extracts were combined and dried over anhydrous magnesium sulfate. Concentration on a rotavaporator and chromatography on a silica gel column with hexane-ether (2:1) gave Δ$^9$-THC-9-carboxylic acid-d$_3$5b (1.43 g), as a colorless liquid, in 92% yield.

Rf: 0.53 hexane-ether (1:1).

$[\alpha]^{23}d$-109.8°(c, 0.00839 g/mL, CHCl$_3$).

IR(neat): 3600–2300, 2920, 2860, 2220, 2060, 1680, 1610, 1570, 1420, 1280, 1260, 840 cm$^{-1}$.

$^1$H NMR(300 MHz, CDCl$_3$): 8.05 (d, J=0.9 Hz, 1 H); 6.31 (d, J=0.6 Hz, 1 H); 6.25 (d, J=0.6 Hz, 1 H); 3.27 (d J=10.5 Hz, 1 H); 2.61–2.53 (m, 2 H); 2.46 (dd, J=7.2 Hz, 7.5 Hz, 2 H); 2.06–2.00 (m, 1 H); 1.71 (dd, J=11.1 Hz, 11.5 Hz, 1 H); 1.59–1.52 (m, 2 H); 1.44 (s, 3 H); 1.31–1.30 (m, 4 H); 1.11 (s, 3 H); 1.00 (s, 9 H); 0.31 (s, 3 H); 0.18 (s, 3 H).

$^{13}$C NMR(75 MHz, CDCl$_3$): 172.98, 154.59, 154.29, 146.18, 142.89, 128.14, 111.38, 110.52, 110.45, 76.83, 44.41, 35.61, 34.92, 31.35, 30.66, 27.46, 25.88, 25.00, 24.28, 22.26, 18.90, 18.25, –3.64, –4.15.

MS: 461 (M$^+$, 1%), 416 (3%), 376 (2%), 308 (4%), 263, 189, 118 (19%), 105 (25%), 75 (83%), 69 (100%).

Exact mass: Calcd. for C$_{27}$H$_{39}$D$_3$O$_4$Si: 461.3041; found: 460.3058.

EXAMPLE 22

GC-MS Assay for THC Metabolites in Urine Using THC Glucuronides as Internal Standards An aliquot of a biological fluid, i.e., 5 mL of a urine specimen to be tested, is mixed in a tube with 20 μl of a methanolic 10 μg/mL solution of 5'-tri-deutero-11-nor-Δ$^9$-THC-9- carboxylic acid glucuronide (i.e., 200 ng/5 mL; resulting concentration in the urine sample is 40 ng/mL as the glucuronide and approximately 26.5 ng/mL as the free acid, after hydrolysis of the THC glucuronide ester in the sample). [Note that the molecular weight of the $d_3$-THC carboxylic acid is 347 gm/mole; and that of the $d_3$-THC carboxylic acid glucuronide is 523 gm/mole.] This is a convenient final concentration of the THC carboxylic acid and THC glucuronide since the "diagnostic standard" presently "confirms" the presence of cannabinoids in urine if a concentration of 15 ng/mL is detected, i.e., as expressed as ng/mL of the free THC carboxylic acid.)

In a separate series of tubes one or more "standards" are prepared by mixing a suitable volume, i.e. 5 mL, of a "blank" solution, i.e., a non-deuterated glucuronide in distilled water sufficient in amount to achieve a final solute concentration in the range of about 10 ng/mL to 60 ng/mL, and 200 ng of the deuterated THC glucuronide, (i.e., 20 µL of the 10 µg/mL methanolic solution, above).

In other tubes a series of "control" urine solutions is prepared by mixing a suitable volume, (i.e., 5 mL), of a control urine with a non-deuterated glucuronide, (i.e., sufficient in amount to achieve a final solute or analyte concentration in the range of about 10 ng/mL to 60 ng/mL in a negative control (uncontaminated) urine sample), and 200 ng of the deuterated THC glucuronide, (i.e., the 20 µL of the 10 µg/mL methanolic solution, above).

The "unknown", "standard", and "control" urine solution is then treated in one of two alternative ways: namely, 1) the THC compounds in the respective tubes are extracted with an organic solvent, dried, and directly derivatized for GC-MS; or, 2) the samples in the respective tubes are first hydrolyzed chemically (or enzymatically) and then extracted with the organic solvent, dried, and derivatized for GC-MS. The organic extracts from the respective specimen, standard, and control samples may be evaporated to dryness to concentrate the THC compounds prior to analysis, or in certain cases it may be desirable not to dry the samples (e.g., in liquid chromotographic methods), but to derivatize them directly for GC-MS. To derivatize the respective dried samples for GC-MS the residue in each tube is vortexed with 50 µL of MSTFA (N-methyl-N-trimethylsilyl trifluoroacetamide) and allowed to react at 60° C. for 15 minutes. The derivatized mixture is then directly analyzed by gas chromatography-mass spectrometry (GC-MS).

The following conditions are typical for the GC-MS analysis of a hydrolyzed THC carboxylic acid. (Those skilled in the art will recognize that suitable conditions may be optimized for GC-MS analysis of the hydrolyzed-derivatized THC carboxylic acid glucuronides and that the following conditions and calculations are illustrative examples.)

GC-MS Conditions:

Instrument: Hewlett Packard, HP-MSD

Column: 20 m/0.18 mm/0.4 µm-DB1

Carrier Gas: Helium

Oven Temperature: 230°–300° C./min.

Ions to be Monitored: $d_3$ –374,476,491; $d_0$–371, 473,488

Quant. Ions: $d_3$ –374; $d_0$–371

Calculation of concentration of THC glucuronide in a specimen is commonly determined by an isotope dilution technique, i.e., a technique in which a sample of the specimen and a sample of a standard are analyzed by GC-MS, the deuterium in the GC-MS column effluent is monitored and allows peak mass to be quantified, i.e., the peak mass of the 371 and 374 peaks. The concentration of the THC compounds in the specimen is then determined by comparing the peak masses of the standard with the specimen, and calculating the proportion of the standard peak mass occupied by the specimen, e.g., using the following calculations:

$$AR = \frac{\text{Area of Chrom. peak mass 371}}{\text{Area of Chrom. peak mass 374}}$$

$$\text{Conc.}_{UNK} = (AR_{std}/AR_{unk})(\text{Conc.}_{STD})$$

where, AR is the relative area; Area of Chrom. peak mass, is the area under the GC-MS curve at peak 371 or 374; Conc.$_{UNK}$, is the calculated concentration of the unknown; AR$_{std}$, is the relative area calculated from the chromatogram of the deuterated standard. The isotope dilution assay for comparing the specimen with the standard is performed either simultaneously, (i.e., as when the deuterated standard is added to the specimen, as an internal standard above), or sequentially, (i.e., when one or more standard solutions, above, are compared with a specimen). When the standard is run on GC-MS at a different time but under identical conditions to the specimen AR$_{unk}$, is the relative area calculated from the chromatogram of the unknown and, Conc.$_{STD}$, is the concentration of standard added to the specimen sample. Generally, the analytical range of the assay (e.g., 10 ng/mL to 60 ng/mL final concentration, above) is selected such that the ratio of the area of $d_0$ (i.e., at 371) to $d_3$ (i.e., at 374), above, do not vary significantly over the range, and thus, are essentially independent of mass ratio. If such a dependence is noted, then the area ratio is plotted in a linear fashion with mass ratio.

As an alternative to an isotope dilution technique for quantifying glucuronide, above, it is also possible to construct a calibration standard curve, (if so desired), through the use of the multiple standards, i.e., described above.

An important aspect of an assay using a THC glucuronide standard is that the % recovery of a deuterated internal standard can be accurately determined, i.e., the % recovery of the deuterium in the GC-MS column effluent of an internal standard in a specimen sample. The percentage recovery can be determined for the sample relative to a standard sample, i.e., deuterated and undeuterated THC glucuronide in a solvent, above, or relative to a control biological sample, i.e., deuterated and undeuterated THC glucuronide in a control urine, above. In this case the peak masses obtained with the standard (or control) samples provides a value referred to below as the Mass of Glucuronide exp.__, i.e., the mass of glucuronide expected, and the % recovery can be calculated as follows:

$$\% \text{ Recovery} = \frac{\text{Mass of Glucuronide exp.-}}{\text{Mass of Glucuronide obs.}} \times 100$$

where exp., is the expected peak mass of glucuronide, and obs., is the observed peak mass of glucuronide in the sample.

The % recovery is useful for: a) correcting the Conc.$_{UNK}$ value (i.e., ng/mL THC metabolites) calculated for a specimen sample to account for variations in technique such as during extraction or hydrolysis; b) adjusting the conditions of the assay to improve the % recovery with a given specimen sample; and, c) adjusting the lower detection limits of the assay up or down until an acceptable % recovery is achieved. An example of how % recovery may be used to correct the Conc.$_{UNK}$ is provided by the following calculation:

$$\text{Conc.}_{specimen} = [\text{Conc.}_{UNK}] * [1/(\% \text{ recovery})(10^{-2})]$$

where, Conc.$_{specimen}$ is the corrected concentration of the THC compound in the specimen sample.

It is worthy of note that until now it was not possible to determine the % recovery, and so it has not been possible to assess losses of the THC carboxylic acid glucuronide, e.g., due to instability during refrigerated or frozen storage, precipitation, chemical degradation, or adsorption to plastic and glass surfaces, (i.e., all previous studies have evaluated such parameters for the THC carboxylic acid, not THC glucuronide.) Thus, it has not previously been possible to determine the actual level of a THC glucuronide in a sample.

Specimen samples that may previously have tested negative because of technical problems, (e.g., associated with a poor recovery), can now be re-tested in a stepwise manner with changes being made by the analyst to either, or both of, the assay conditions, (e.g., the hydrolysis or extraction conditions), or the lower detection limits of the assay. For example, the lower detection limits of the assay may be adjusted in a stepwise manner upward or downward until a desired % recovery is achieved.

The detection sensitivity for the assay can be adjusted downward (i.e., into the range of 0.5 to 5 ng/mL) or upward (i.e., into the range of 50 to 500 ng/mL) based upon precise determination of % of Recovery of the non-deuterated THC glucuronide standard. For example, improved low-end sensitivity (i.e., ng/ml at which a positive assay result is recorded greater than 95% of the time), and improved assay precision, and reproducibility is obtained by: a) preparing 20 different control samples, as above; b) analyzing the 20 control samples, as above; c) calculating the Conc.$_{UNK}$, as above; calculating the % recovery, as above, and using the calculated % recovery to calculate the Conc.$_{specimen}$, as above; d) calculating the precision and reproducibility of the results obtained in the assay; e) adjusting the low-end sensitivity of the assay downward, i.e., as described above, until either the precision, or reproducibility of the assay begins to deteriorate.

Using THC glucuronides as calibrators (i.e., standard samples, above), standards (i.e., internal standards in biological fluids, above), and controls (i.e., control samples, above) allows the analyst to calculate the % recovery on a sample-by-sample basis, and correct for technical problems that negatively impact the specificity, sensitivity, and precision of assay.

EXAMPLE 23

GC-MS Assay for THC Metabolites in Blood Using THC Glucuronides as Internal Standards The procedures as set forth in Example 22 are also useful for evaluating THC metabolites in blood, fecal matter, hair, and other biological and environmental samples (e.g., soil, clothing, plastic and glass containers and the like). An illustrative example is provided here of how a sample of blood may be assayed.

The same procedure as set forth in Example 22 is employed except smaller volumes of blood are required and these samples are preferably first clotted or centrifuged to obtain serum or plasma. Protein in the serum or plasma sample is then conveniently precipitated by adding 5 mL of an organic solvent, i.e., acetonitrile. The 11-nor-$\Delta^9$-THC-9-carboxylic acid glucuronide internal standard is conveniently added to the specimen in the organic solvent. The precipitate is conveniently collected by centrifugation (or filtration) and the supernatant is transferred to another tube. The precipitate is extracted for a second time with another aliquot of the organic solvent. After re-centrifugation of the precipitate the second supernatant is combined with the first and evaporated to dryness. The sample is then analyzed by GC-MS as set forth in Example 22, above.

EXAMPLE 24

Preparation of THC Glucuronide Specific Antibodies

THC glucuronides are haptens that are rendered immunogenic by coupling to a suitable protein carrier, e.g., ovalbumin, Key Hole Limpet hemocyanin (KLH), thyroglobulin, and the like. It is important in this regard that care be excercised in the choice of coupling agent and method so that the glycal group of the THC glucuronide is left accessible (i.e., in three-dimensional space) for immune recognition and antibody binding. In this regard, the 1' to 5' hydrocarbon chain of THC is a desirable location through which to couple THC glucuronides to a carrier. In particular, the 5' ethoxy compound 28 or 3' keto compound 29 shown in Examples 12 and 13, respectively, show examples of chemically reactive groups that can be introduced into the 1' to 5' hydrocarbon chain for the purpose of coupling to a carrier. In this case, linkage to the carrier is conveniently achieved by forming an ester, ether, peptide, or amide bond with a suitable reactive group in the protein carrier. Coupling is easily accomplished, e.g., with an N-hydroxysuccinimide derivative of a 5' carboxylate or using a heterobifunctional linker.

Polyclonal and monoclonal antibodies are conveniently produced by injecting 10 µg–10 mg of a THC glucuronide hapten-carrier conjugate at bi-weekly intervals in a suitable adjuvant, (e.g., Freund's complete or incomplete adjuvant, purified myristoyl lipids from Bacillus Calmette Guerin and the like), into each of 4 subcutaneous sites in a rabbit (for polyclonal) or mouse (for monoclonal). The animals are test bled on alternate weeks and their serum is tested for the presence of antibodies that bind to THC glucuronide, (i.e., 11-nor $\Delta^9$-THC-9-carboxylic acid glucuronide) to a greater extent than THC carboxylic acid, (i.e., 11-nor-$\Delta^9$-THC-9-carboxylic acid). This testing is conveniently accomplished in an enzyme-linked immunoadsorbent assay (ELISA) by:

a) coating microtiter ELISA plates (e.g., Dynatek II plates) with either 100 µl of a THC-carboxylic acid or THC-glucuronide, e.g., (100 ng-100 µg/ml) in distilled water, methanol, dioxane, or other suitable solvent;

b) blocking un-bound sites, (e.g., with ovalbumin, or milk proteins in 10 mM sodium phosphate buffered, pH 7.2, 0.14M saline (PBS) containing 1% Tween 20;

c) placing dilutions of the serum sample in the respective test wells; and, d) measuring binding of serum antibodies to the THC compound in the well by adding enzyme-conjugated, (e.g., horse radish peroxidase; HRP) anti-rabbit or anti-mouse IgG for 60 minutes. (After 60 minutes, un-bound second antibody is removed by washing, e.g., with PBS, 1% Tween 20), and bound second antibody is visualized by adding an enzyme substrate (e.g., ABTS, Sigma Chem. Co., St. Louis, Mo.) and incubating 30–45' to allow color development.)

In immunoassay (e.g., ELISA) the presence of serum antibodies reactive with THC glucuronide, but not THC carboxylic acid, is recognized by the presence of a greater signal (e.g., color) at a greater dilution of serum when tested on the THC glucuronide antigen than when tested on the THC carboxylic acid. For example, a color of 0.5 units at a dilution of 1:8 when the serum dilution is placed in microtiter plates coated with THC glucuronide as compared with a signal of 0.1 units when the same serum dilution is tested on the THC carboxylic acid. Rabbits that have serum that exhibit this property of greater binding to THC glucuronide are useful for preparation of affinity-purified anti-THC glucuronide, as described below. Mice that have serum exhibiting this property of greater binding to THC glucuronide are useful for preparation of monoclonal antibodies, as described below.

Affinity purification of polyclonal antibodies is conveniently accomplished by coupling 1 mg of THC carboxylic acid (i.e., 11-nor-$\Delta^9$ THC carboxylic acid), or 1 mg of THC glucuronide (i.e., 11-nor-$\Delta^9$ THC glucuronide), to each of two different insoluble supports such as 50 ml each of cyanogen-bromide activated Sepharose (Pharmacia, Piscatawy, N.J.). the THC carboxylic acid-Sepharose and THC glucuronide Sepharose are then used to prepare two affinity columns. Affinity purification of antibodies reactive with THC glucuronide but not THC carboxylic acid is accomplished in two steps. First, fifty to seventy-five ml of ELISA positive rabbit serum is passed over the THC carboxylic acid-Sepharose column and the column eluate is collected and tested again in the ELISA assay, as above. Successful affinity purification in this first step is achieved when less than 0.100 units of color are developed in microtiter wells containing bound THC carboxylic acid, and when the signal in the THC glucuronide containing wells is greater than 0.200 units of color. If these criteria are met, the column eluate from the first step is suitable for the second step of affinity purification. Second, the column eluate from step 1 is placed onto the THC glucuronide column and the column is washed, e.g., with PBS, pH 7.2, until the optical density at 280 nm is less than 0.05. Specifically bound antibodies are eluted at low pH, e.g., in glycine-HCL buffer, pH 3, into 10 mM Tris buffer, pH 7 and the eluted antibodies are once again tested for specificity of binding in the ELISA. A suitable preparation has been achieved when a dilution of the low pH eluate a) gives less than 0.100 units of color with THC carboxylic acid; and b) gives a color of greater than 0.500 units with THC glucuronide. For example, if these criteria are met in a low pH eluate diluted more than 1:20 then this antibody reagent is suitable for use if diluted more than 1:20.

Selection of monoclonal antibodies is achieved by sacrificing mice whose serum has tested positive for THC-glucuronide specific antibodies, e.g., in the ELISA, above. Immune splenic lymphocytes are prepared from these animals by mincing and screening the spleen to prepare a cellular suspension. After centrifugal purification, the immune spleen cells are fused with a suitable non Ig-producer HPRT-sensitive murine myeloma (i.e., NS-1 or X63-Ag8) according to well established methods (45). After selection in HAT medium and cloning by limiting dilution (45), supernatant culture medium from the resultant hybridomas is tested in the ELISA assay, described above. A hybridoma is suitable for subcloning and additional characterization if the culture medium exhibits less than 0.100 units of color at a dilution of 1:2 on THC carboxylic acid and greater than 0.300 units of color on THC glucuronide at the same dilution. If these criteria are met the hybridoma culture may be suitable for further subcloning and testing to select a THC glucuronide specific monoclone producing antibody that binds to THC glucuronide but not THC carboxylic acid.

Citations

1. Williams et al. J. Pharm. Pharmacol. 32: 445 (1980)
2. Razdan et al. J. Am. Chem. Soc. 96: 5860 (1974)
3. Hardrick et al. Tetrahedron Lett 681 (1979)
4. Mechoulam et al. J. Am. Chem. Soc. 94: 6159 (1972)
5. Mechoulam et al. J. Am. Chem. Soc. 94: 7930 (1972)
6. Petrzilka et al. Helv. Chim. Acta 50: 719 (1967)
7. Petrzilka et al. Helv. Chim. Acta 52: 1102 (1969)
8. Rickards et al. 1. Org. Chem. 49: 572 (1984)
9. Childers et al. J. Org. Chem.49: 5276 (1984)
10. Schwartz et al. J. Org. Chem. 51: 5463 (1986)
11. Archer et al. "Cannabinoids as Therapeutic Agents", ed. R. Mechoulam, CRC Press, Boca Raton, Fla. 1986. pp.85–103.
12. Pallante et al. Drug Metab. and Disposition 6: 389 (1978)
13. Tius et al. J. Chem. Soc., Chem. Commun. 62 (1989)
14. Faed, et al. Drag Metab. Res. 15: 1213 (1984)
15. Keglevic, D. Adv. Carbohydr. Chem. Biochem. 36: 57 (1979)
16. Caldwell, J. Drug Metab. Res. 13: 745 (1982)
17. Cook, C. E. In: Cannabinoid Analysis in Physiological Fluids, A.C.S. Symposium Series 98, Vinson, J. A. Ed. A.C.S., Wash. D.C. 1979, pp. 137–154.
18. Teate, J. D. Laucet 2: 553 (1974)
19. Chase et al. In: Cannabinoid Assays in Humans, NIDA Research Monograph, No. 7, Willette, R. Ed., V.S.D.H.E.W., Wash. D.C. 1976, pp. 1–9.
20. Jones, A. et al. J. Anal. Toxicol. 8: 252 (1984)
21. Rowley, G. et al. In: Cannabinoid Assays in Humans, supra, pp.28–32
22. Rodgers, R. et al. Clin. Chem. 24: 95 (1978)
23. O'Connor et al. J. Anal. Toxicol. 5: 168 (1981)
24. Law et al. J. Anal. Toxicol. 8: 14 (1984)
25. Childs et al. J. Anal. Toxicol. 8: 220 (1984)
26. McNally et al. U.S. Pat. No. 4,833,073
27. Wang et al. European Patent Application No. 90111061.9
28. Kaufman et al. European Patent Application No. 90106444.4
29. Fahrenholt et al. U.S. Pat. No. 4,438,207.
30. Gross et al. U.S. Pat. No. 4,022,878.
31. Cook et al. NIDA Research Monograph No. 7: 15 (1976).
32. Teale et al. Nature 249: 154 (1974).
33. Grant yet al. Nature New Biol. 236: 216 (1972).
34. Teale et al. J. Pharmacol. and Pharmaceutics 27: 465 (1975).
35. Nordgrist, M. et al. In: Cannabinoid Assays in Humans, supra, pp.64–69
36. Karlsson, L. et al. I. Anal. Toxicok 7: 198 (1983)
37. Foltz, R. L. et al. Biomed Mass Spectrom. 10: 316 (1983)
38. Halcomb, R. L. and S. I. Danishefsky, *J. Am. Chem. Soc.,* 111: 6661–6666, 1989.
39. Narasaka, K., A. Morikawa, K. Salgo and T. Mukaiyama, *Bull. Chem. Soc. Japan,* 50: 2773–2776, 1977.
40. Plusquellec, D., F. Roulleau, F. Bertho, M. Lefeuvre and E. Brown, *Tetrahedron,* 42: 2457–2467, 1986.
41. Kanaoka, M., S. Yano, H. Kato and T. Nakada, *Chem. Pharm. Bull.,* 34: 4978–4983, 1986.
42. Keglevic, D., and D. Ljevakovic, *Carbohydr. Res.,* 64: 319–322, 1978.
43. Pravdic, N., and D. Keglevic, *Tetrahedron,* 21: 1897–1901, 1965.
44. Grynkieweicz, G., Fokt, L., Szeja, W. and H. Fitak, *J. Chem. Research* (S): 152–153, 1989.
45. Schrier et al. Hybridoma Techniques, Cold Spr. Harbor Lab., Cold Spr. N.Y. 1980.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing a carboxylic acid glucuronide comprising reacting a carboxylic acid precursor with a dual-blocked sugar epoxide precursor of the formula:

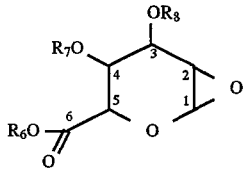

wherein $R_6$ is a first protective agent, and $R_7$ and $R_8$ are a second protective agent, to obtain a dual-blocked carboxylic acid glucuronide precursor; and then removing the first and the second protective agents from the dual-blocked sugar epoxide precursor to obtain a carboxylic acid glucuronide of the formula:

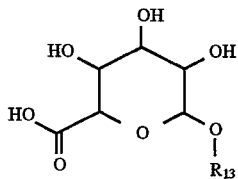

wherein $R_{13}$ is the acyl residue of said carboxylic acid precursor.

2. The method of claim 1, wherein the first protective agent is selected from the group consisting of benzyl, methoxybenzyl, dimethoxybenzyl, linnamyl, allyl, methallyl, trityl, fluorenyl, and diphenylmethyl groups.

3. The method of claim 1, wherein the second protective agent is selected from the group consisting of tert-butyl dimethyl silyl, tert-butyl dimethyl allyl, t-hexyldimethylsilyl, triethylsilyl, and tri-isopropylsilyl.

4. The method of claim 1 wherein the dual-blocked sugar epoxide precursor is produced by the steps comprising:

forming a 1,2 glycal having one or more reactive carboxyl, acetyl, or aldehyde groups and one or more reactive hydroxyl groups;

blocking one or more of the reactive carboxyl, acetyl, or aldehyde groups with the first protective agent; blocking one or more of the reactive hydroxyl groups with a second protective agent; and then treating the blocked glycal with a dioxirane to form the dual-blocked sugar epoxide.

5. The method of of claim 1 wherein the the first and second protective agents removed by the steps comprising:

a) reacting the dual-blocked glucuronide precursor with HF and $CH_3CN$ to form a mono-blocked glucuronide precursor; and, b) catalytically hydrogenating the mono-blocked glucuronide precursor.

* * * * *

UNITED STATES PATENT AND TRADEMARK OFFICE
CERTIFICATE OF CORRECTION

PATENT NO. : 5,633,357
DATED : May 27, 1997
INVENTOR(S) : M.A. Tius et al.

It is certified that error appears in the above-indentified patent and that said Letters Patent is hereby corrected as shown below:

| COLUMN | LINE | |
|---|---|---|
| 1 | Refs. Cited U.S. Patents Item #1 | After "Ramsden" insert --et al.-- |
| 1 | Refs. Cited Other Publs. Item #1 | Before "*Pharmacol.*" insert --*Pharm.*-- |
| 38 | 17 | After "agent;" begin a new subparagraph with "blocking" |
| 38 | 23 | After "agents" insert --are-- |

Signed and Sealed this

Twenty-sixth Day of May, 1998

Attest:

*Attesting Officer*

BRUCE LEHMAN
*Commissioner of Patents and Trademarks*